US007727532B2

(12) United States Patent
Thomas, Jr. et al.

(10) Patent No.: US 7,727,532 B2
(45) Date of Patent: Jun. 1, 2010

(54) HUMAN ANTIBODIES AGAINST RABIES AND USES THEREOF

(75) Inventors: William D. Thomas, Jr., Somerville, MA (US); Donna M. Ambrosino, Jamaica Plain, MA (US); Robert Mandell, Collins, IA (US); Susan Sloan, Jamaica Plain, MA (US); Gregory J. Babcock, Marlborough, MA (US); Charles Rupprecht, Lawrenceville, GA (US)

(73) Assignees: University of Massachusetts, Boston, MA (US); Centers for Disease Control and Prevention, Atlanta, GA (US)

( * ) Notice: Subject to any disclaimer, the term of this patent is extended or adjusted under 35 U.S.C. 154(b) by 90 days.

(21) Appl. No.: 11/890,317

(22) Filed: Aug. 2, 2007

(65) Prior Publication Data

US 2009/0041777 A1    Feb. 12, 2009

Related U.S. Application Data

(63) Continuation of application No. PCT/US2006/003644, filed on Feb. 2, 2006.

(60) Provisional application No. 60/649,512, filed on Feb. 2, 2005.

(51) Int. Cl.
*A61K 39/42*     (2006.01)
*A61K 39/205*    (2006.01)

(52) U.S. Cl. .................. 424/159.1; 424/224.1

(58) Field of Classification Search ............ None
See application file for complete search history.

(56) References Cited

U.S. PATENT DOCUMENTS

| | | | | |
|---|---|---|---|---|
| 5,840,300 A | * | 11/1998 | Williams et al. | 424/135.1 |
| 2003/0165507 A1 | * | 9/2003 | Hooper et al. | 424/147.1 |

FOREIGN PATENT DOCUMENTS

| | | |
|---|---|---|
| WO | WO-95/09249 A1 | 4/1995 |
| WO | WO-01/88132 A2 | 11/2001 |
| WO | WO-02/094880 A1 | 11/2002 |
| WO | WO-2005/002511 A2 | 1/2005 |
| WO | WO-2005/023849 A2 | 3/2005 |

OTHER PUBLICATIONS

Rudikoff et al. PNAS USA, 1982, 79:1979-1983.*
MacCallum et al. J. Mol. Biol. 1996, 262:732-745.*
De Pascalis et al. The Journal of Immunology, 2002, 169:3076-3084.*
Casset et al. BBRC, 2003, 307:198-205.*
Prehaud, Christophe et al., "Immunogenic and Protective Properties of Rabies Virus Glycoprotein Expressed by Baculovirus Vectors," *Virology*, vol. 173:390-399 (1989).
Sloan, Susan E. et al., "Identification and characterization of a human monoclonal antibody that potently neutralizes a broad panel of rabies virus isolates," *Vaccine*, vol. 25:2800-2810 (2007).
Benmansour, A. et al., "Antigenicity of Rabies Virus Glycoprotein," *Journal of Virology*, vol. 65(8):4198-4203 (1991).
Champion, J.M. et al., "The development of monoclonal human rabies virus-neutralizing antibodies as a substitute for pooled human immune globulin in the prophylactic treatment of rabies virus exposure," *Journal of Immunological Methods*, vol. 235:81-90 (2000).
Cox, James H. et al., "Rabies Virus Glycoprotein, II. Biological and Serological Characterization," *Infection and Immunity*, vol. 16(3):754-759 (1977).
Dietzschold, Bernhard et al., "Biological Characterization of Human Monoclonal Antibodies to Rabies Virus," *Journal of Virology*, vol. 64(6):3087-3090 (1990).
Hanlon, C.A. et al., "The incurable wound revisited: progress in human rabies prevention?" *Vaccine*, vol. 19:2273-2279 (2001).
Irie, Takashi et al., "Studies on the Escape Mutants of Rabies Virus Which Are Resistant to Neutralization by a Highly Conserved Conformational Epitope-Specific Monoclonal Antibody #1-46-12," *Microbiol. Immunol.*, vol. 46(7):449-461 (2002).
Kankanamge, Pushpa Jenette et al., "Mapping of the Low pH-Sensitive Conformational Epitope of Rabies Virus Glycoprotein Recognized by a Monoclonal Antibody #1-30-44," *Microbiol. Immunol.*, vol. 47 (7):507-519 (2003).
Marissen, Wilfred E. et al., "Novel Rabies Virus-Neutralizing Epitope Recognized by Human Monoclonal Antibody: Fine Mapping and Escape Mutant Analysis," *Journal of Virology*, vol. 79(8):4672-4678 (2005).
Rando, R.F. et al., "Production of Human Monoclonal Antibodies Against Rabies Virus," *Current Topics in Microbiology and Immunology*, vol. 187:195-205 (1994).
Ray, K. et al., "Selection of single chain variable fragments (scFv) against the glycoprotein antigen of the rabies virus from a human synthetic scFv phage display library and their fusion with the Fc region of human IgG1," *Clin. Exp. Immunol.*, vol. 125:94-101 (2001).
International Search Report for Application No. PCT/US2006/003644, dated Jul. 12, 2006.
International Preliminary Report on Patentability for Application No. PCT/US2006/003644, dated Feb. 22, 2007.
Written Opinion for Application No. PCT/US2006/003644, dated Jul. 12, 2006.
EMBL AC M18517, "Human (fetal) Ig rearranged H-chain VDJ-region mRNA, clone 56P1," (2007).
Geneseq AC ABZ59699, "Anti-Trail-R antibody related clone 0304 nucleotide SEQ ID No:30," (2003).
Schroeder, Harry W. Jr. et al., "Early Restriction of the Human Antibody Repertoire," *Science*, vol. 238(4828):791-793 (1987).

* cited by examiner

*Primary Examiner*—Stacy B Chen
(74) *Attorney, Agent, or Firm*—Lahive & Cockfield, LLP; Jane E. Remillard, Esq.; Jilly Gorny Sloper, Esq.

(57) ABSTRACT

Human monoclonal antibodies that specifically bind to rabies virus, antigen binding portions thereof, and methods of making and using such antibodies and antigen binding portions thereof for treating rabies virus in a subject, are provided herein.

26 Claims, 9 Drawing Sheets

FIG. 1

AMINO ACID SEQUENCE OF EXEMPLARY ANTI-RABIES HUMAN 17C7 ANTIBODY VARIABLE REGION heavy chain variable region (17C7 VH)
(SEQ ID NO: 1)

```
leader                                              CDR 1
MEFGLNWVFLVALLRGVQCQVQLVESGGGVVQPGRSLRLSCAASGFTFSTYAMHWVRQAP 60
            CDR 2                          (SEQ ID NO: 3)
GKGLEWVAVVSYDGRTKDYADSVKGRFTISRDNSKNTLYLQMNSLRTEDTAVYFCARERF 119
   CDR 3     (SEQ ID NO: 4)
SGAYFDYWGQGTLVTVSSASTKGP 144
(SEQ ID NO: 5)
``` light chain variable region (17C7 VL)
(SEQ ID NO: 2)

```
leader                                              CDR 1
MEAPAQLLFLLLLWLPDTTGEIVLTQSPATLSLSPGERATLSCRASQSVSSYLAWYQQKP 60
            CDR 2                       (SEQ ID NO: 6)  CDR 3
GQAPRLLIYDASNRATGIPARFSGSGSGTDFTLTISSLEPEDFAVYSCQQRNNWPPTFGG 120
   (SEQ ID NO: 7)                              (SEQ ID NO: 8)
GTKVEIK 127
```

FIG. 2

AMINO ACID SEQUENCE OF EXEMPLARY ANTI-RABIES HUMAN 6G11 ANTIBODY VARIABLE REGION heavy chain variable region (6G11 VH)
(SEQ ID NO: 15)

```
leader                                CDR 1                CDR 2
MEFGLSWVFLVALLRGVQC QVQLVESGGGVVQPGRSLRLSCAAS GFTFSSYG MHWVRQAPGKGLEW VAVIL
                                      (SEQ ID NO: 17)     (SEQ ID NO: 18)
                                                CDR 3
YDGSNK YHADSVKGRFTISRDNSKNTLYLQMNSLRAEDTAVYYC ARIAPAGSAFDY WGQGTLVTVSSASTKGP
                                              (SEQ ID NO: 19)
``` light chain variable region (6G11 VL)
(SEQ ID NO: 16)

```
leader                                       CDR 1
MDMMVPAQLLGLLLLWLPGARCA IQLTQSPSSLSASVGDRVTITCRAS QGISSV LAWYQQKSGKAPKFLIY
                                                (SEQ ID NO: 20)
CDR 2                                   CDR 3
DAS SLESGVPSRFSGSGSGTDFTLTISSLQPEDFATYYC QQFNSYPP TFGQGTKLEIK
(SEQ ID NO: 21)                         (SEQ ID NO: 22)
```

FIG. 3

EPITOPE MAPPING OF RABIES VIRUS GLYCOPROTEIN

Schematic of Protein Structure

| clone | a.a. residues | IP | immunoblot |
|---|---|---|---|
| COG524 | 19-524 | + | + |
| COG439 | 19-439 | + | + |
| COG422 | 19-422 | + | + |

FIG. 7
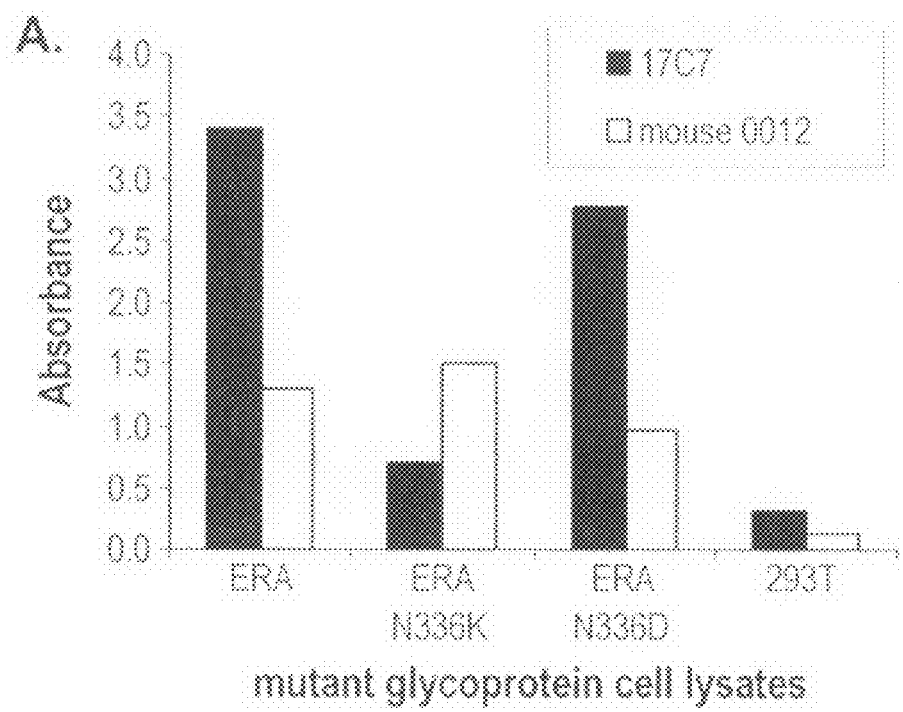
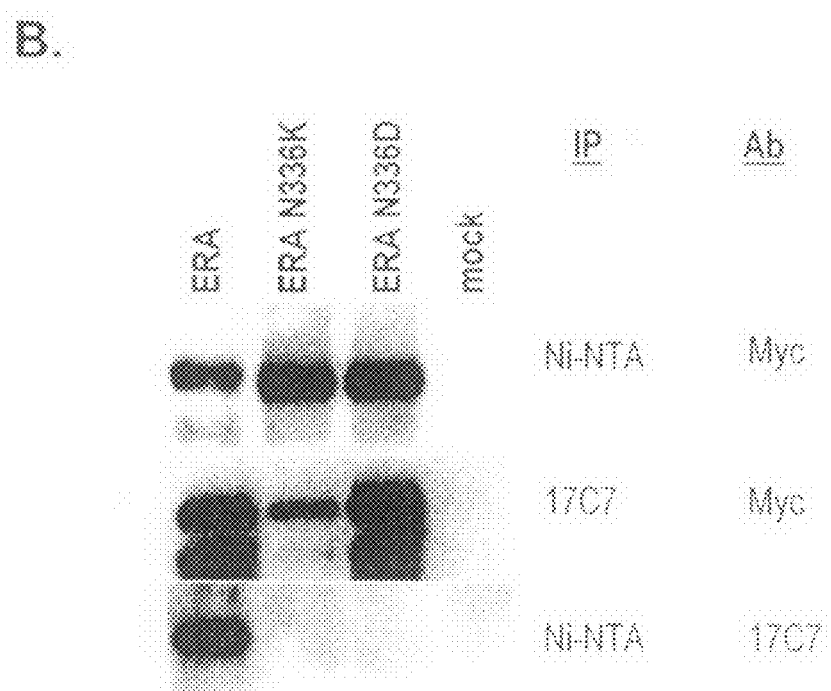

FIG. 9
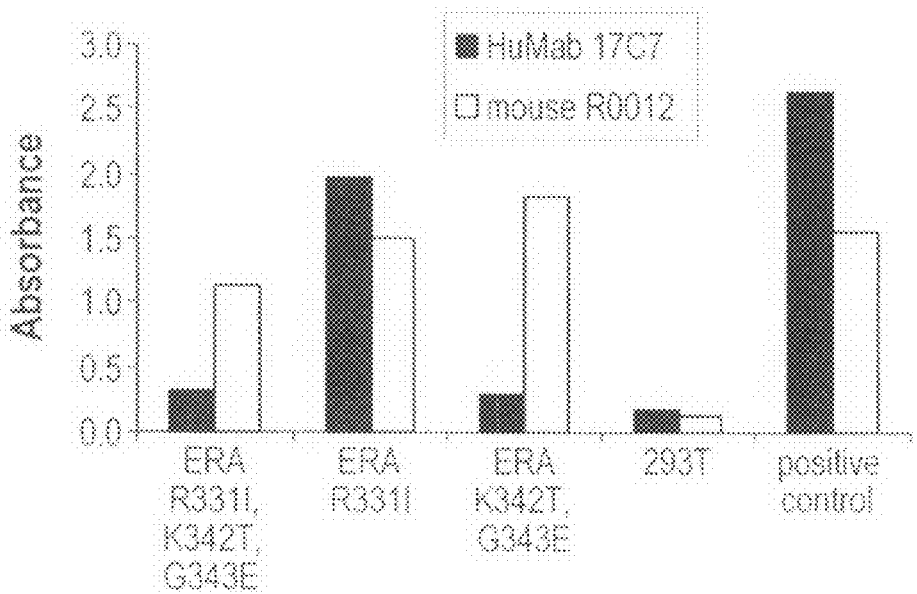
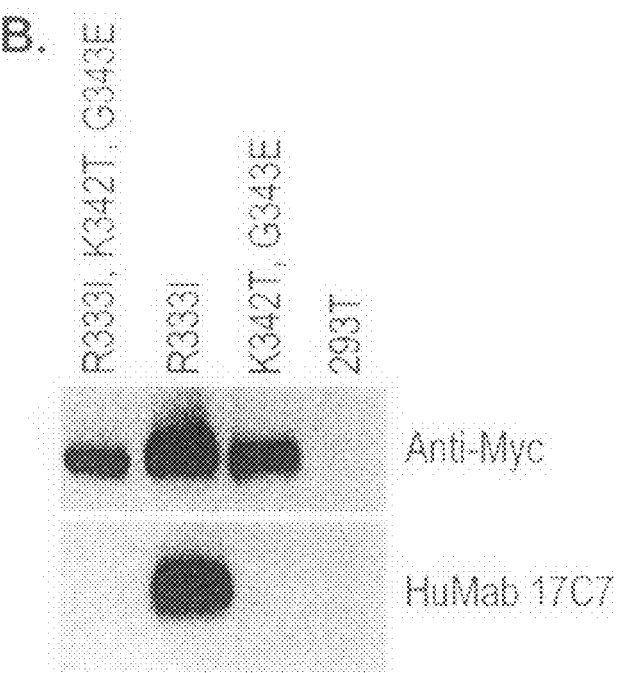

```
                              SEQUENCE LISTING

<160> NUMBER OF SEQ ID NOS: 34

<210> SEQ ID NO 1
<211> LENGTH: 144
<212> TYPE: PRT
<213> ORGANISM: Homo sapiens

<400> SEQUENCE: 1

Met Glu Phe Gly Leu Asn Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Thr Tyr Ala Met His Trp Val Arg Gln Ala Pro Gly Lys Gly Leu
    50                  55                  60

Glu Trp Val Ala Val Val Ser Tyr Asp Gly Arg Thr Lys Asp Tyr Ala
65                  70                  75                  80

Asp Ser Val Lys Gly Arg Phe Thr Ile Ser Arg Asp Asn Ser Lys Asn
                85                  90                  95
```

```
Thr Leu Tyr Leu Gln Met Asn Ser Leu Arg Thr Glu Asp Thr Ala Val
            100                 105                 110

Tyr Phe Cys Ala Arg Glu Arg Phe Ser Gly Ala Tyr Phe Asp Tyr Trp
        115                 120                 125

Gly Gln Gly Thr Leu Val Thr Val Ser Ser Ala Ser Thr Lys Gly Pro
    130                 135                 140

<210> SEQ ID NO 2
<211> LENGTH: 127
<212> TYPE: PRT
<213> ORGANISM: Homo sapiens

<400> SEQUENCE: 2

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Ser Cys Gln Gln Arg Asn
            100                 105                 110

Asn Trp Pro Pro Thr Phe Gly Gly Gly Thr Lys Val Glu Ile Lys
        115                 120                 125

<210> SEQ ID NO 3
<211> LENGTH: 5
<212> TYPE: PRT
<213> ORGANISM: Homo sapiens

<400> SEQUENCE: 3

Thr Tyr Ala Met His
1               5

<210> SEQ ID NO 4
<211> LENGTH: 17
<212> TYPE: PRT
<213> ORGANISM: Homo sapiens

<400> SEQUENCE: 4

Val Val Ser Tyr Asp Gly Arg Thr Lys Asp Tyr Ala Asp Ser Val Lys
1               5                   10                  15

Gly

<210> SEQ ID NO 5
<211> LENGTH: 7
<212> TYPE: PRT
<213> ORGANISM: Homo sapiens

<400> SEQUENCE: 5

Ser Gly Ala Tyr Phe Asp Tyr
1               5

<210> SEQ ID NO 6
<211> LENGTH: 11
```

```
<212> TYPE: PRT
<213> ORGANISM: Homo sapiens

<400> SEQUENCE: 6

Arg Ala Ser Gln Ser Val Ser Ser Tyr Leu Ala
1               5                   10

<210> SEQ ID NO 7
<211> LENGTH: 7
<212> TYPE: PRT
<213> ORGANISM: Homo sapiens

<400> SEQUENCE: 7

Asp Ala Ser Asn Arg Ala Thr
1               5

<210> SEQ ID NO 8
<211> LENGTH: 7
<212> TYPE: PRT
<213> ORGANISM: Homo sapiens

<400> SEQUENCE: 8

Gln Gln Arg Asn Asn Trp Pro
1               5

<210> SEQ ID NO 9
<211> LENGTH: 705
<212> TYPE: DNA
<213> ORGANISM: Homo sapiens
<220> FEATURE:
<223> OTHER INFORMATION: synthetic construct

<400> SEQUENCE: 9
atggaagccc cagctcagct tctcttcctc ctgctactct ggctcccaga taccaccgga      60
gaaattgtgt tgacacagtc tccagccacc ctgtctttgt ctccagggga aagagccacc    120
ctctcctgca gggccagtca gagtgttagc agctacttag cctggtacca acagaaacct    180
ggccaggctc ccaggctcct catctatgat gcatccaaca gggccactgg catcccagcc    240
aggttcagtg gcagtgggtc tgggacagac ttcactctca ccatcagcag cctagagcct    300
gaagattttg cagtttattc ctgtcagcag cgtaacaact ggcctcccac tttcggcgga    360
gggaccaagg tggagatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga aaacacaaa gtctacgcct gcgaagtcac ccatcagggc    660
ctgagctcgc ccgtcacaaa gagcttcaac aggggagagt gttag                     705

<210> SEQ ID NO 10
<211> LENGTH: 234
<212> TYPE: PRT
<213> ORGANISM: Homo sapiens
<220> FEATURE:
<223> OTHER INFORMATION: synthetic construct

<400> SEQUENCE: 10

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30
```

```
Leu Ser Pro Gly Glu Arg Ala Thr Leu Ser Cys Arg Ala Ser Gln Ser
             35                  40                  45
Val Ser Ser Tyr Leu Ala Trp Tyr Gln Gln Lys Pro Gly Gln Ala Pro
     50                  55                  60
Arg Leu Leu Ile Tyr Asp Ala Ser Asn Arg Ala Thr Gly Ile Pro Ala
 65                  70                  75                  80
Arg Phe Ser Gly Ser Gly Ser Gly Thr Asp Phe Thr Leu Thr Ile Ser
                 85                  90                  95
Ser Leu Glu Pro Glu Asp Phe Ala Val Tyr Ser Cys Gln Gln Arg Asn
            100                 105                 110
Asn Trp Pro Thr Phe Gly Gly Gly Thr Lys Val Glu Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230

<210> SEQ ID NO 11
<211> LENGTH: 1407
<212> TYPE: DNA
<213> ORGANISM: Homo sapiens
<220> FEATURE:
<223> OTHER INFORMATION: synthetic construct

<400> SEQUENCE: 11
atggagtttg ggctgaactg gttttcctc gttgctcttt taagaggtgt ccagtgtcag    60
gtgcagctgg tggagtctgg gggaggcgtg gtccagcctg gaggtccct gagactctcc   120
tgtgcagcct ctggattcac cttcagtacc tatgctatgc actgggtccg ccaggctcca   180
ggcaagggc tggagtgggt ggcagttgta tcatatgatg gacgcactaa agactacgca   240
gactccgtga agggccgatt caccatctcc agagacaatt ccaagaacac gctgtatctg   300
caaatgaaca gcctgagaac tgaggacacg gctgtgtatt tctgtgcgag agagaggttc   360
tctgggcct actttgacta ctggggccag ggaaccctgg tcaccgtctc ctcagcctcc   420
accaagggcc catcggtctt ccccctggca cctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc   660
tgcaacgtga atcacaagcc cagcaacacc aaggtggaca gagagttga gcccaaatct   720
tgtgacaaaa ctcacacatg cccaccgtgc ccagcacctg aactcctggg gggaccgtca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
```

```
gacggcgtgg aggtgcataa tgccaagaca aagccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga ggagatgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctatagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatag                                       1407
```

<210> SEQ ID NO 12
<211> LENGTH: 468
<212> TYPE: PRT
<213> ORGANISM: Homo sapiens
<220> FEATURE:
<223> OTHER INFORMATION: synthetic construct

<400> SEQUENCE: 12

```
Met Glu Phe Gly Leu Asn Trp Val Phe Leu Val Ala Leu Leu Arg Gly
  1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Ser Thr Tyr Ala Met His Trp Val Arg Gln Ala Pro Gly Lys Gly Leu
     50                  55                  60

Glu Trp Val Ala Val Val Ser Tyr Asp Gly Arg Thr Lys Asp Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Thr Glu Asp Thr Ala Val
            100                 105                 110

Tyr Phe Cys Ala Arg Glu Arg Phe Ser Gly Ala Tyr Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270
```

```
Met Ile Ser Arg Thr Pro Glu Val Thr Cys Val Val Asp Val Ser
        275                 280                 285
His Glu Asp Pro Glu Val Lys Phe Asn Trp Tyr Val Asp Gly Val Glu
    290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Glu Glu Met Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
    450                 455                 460
Ser Pro Gly Lys
465

<210> SEQ ID NO 13
<211> LENGTH: 432
<212> TYPE: DNA
<213> ORGANISM: Homo sapiens

<400> SEQUENCE: 13
atggagtttg ggctgaactg ggttttcctc gttgctcttt taagaggtgt ccagtgtcag     60
gtgcagctgg tggagtctgg gggaggcgtg gtccagcctg gaggtccct gagactctcc    120 tgtgcagcct ctggattcac cttcagtacc tatgctatgc actgggtccg ccaggctcca    180
ggcaaggggc tggagtgggt ggcagttgta tcatatgatg gacgcactaa agactacgca    240
gactccgtga agggccgatt caccatctcc agagacaatt ccaagaacac gctgtatctg    300
caaatgaaca gcctgagaac tgaggacacg gctgtgtatt tctgtgcgag agagaggttc    360 tctgggcct actttgacta ctgggccag ggaaccctgg tcaccgtctc ctcagcctcc    420
accaagggcc ca                                                       432

<210> SEQ ID NO 14
<211> LENGTH: 381
<212> TYPE: DNA
<213> ORGANISM: Homo sapiens

<400> SEQUENCE: 14
atggaagccc agctcagct tctcttcctc ctgctactct ggctcccaga taccaccgga     60
gaaattgtgt tgacacagtc tccagccacc ctgtctttgt ctccagggga aagagccacc    120
ctctcctgca gggccagtca gagtgttagc agctacttag cctggtacca acagaaacct    180
ggccaggctc ccaggctcct catctatgat gcatccaaca gggccactgg catcccagcc    240
```

```
aggttcagtg gcagtgggtc tgggacagac ttcactctca ccatcagcag cctagagcct    300
gaagattttg cagtttattc ctgtcagcag cgtaacaact ggcctcccac tttcggcgga    360
gggaccaagg tggagatcaa a                                              381
```

```
<210> SEQ ID NO 15
<211> LENGTH: 125
<212> TYPE: PRT
<213> ORGANISM: Homo sapiens

<400> SEQUENCE: 15
```

| Gln | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Gly | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Val | Ile | Leu | Tyr | Asp | Gly | Ser | Asn | Lys | Tyr | His | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Ile | Ala | Pro | Ala | Gly | Ser | Ala | Phe | Asp | Tyr | Trp | Gly | Gln | Gly |
|---|---|---|---|---|---|---|---|---|---|---|---|---|---|---|---|
| | | | 100 | | | | | 105 | | | | | 110 | | |

| Thr | Leu | Val | Thr | Val | Ser | Ser | Ala | Ser | Thr | Lys | Gly | Pro |
|---|---|---|---|---|---|---|---|---|---|---|---|---|
| | | 115 | | | | | 120 | | | | | 125 |

```
<210> SEQ ID NO 16
<211> LENGTH: 107
<212> TYPE: PRT
<213> ORGANISM: Homo sapiens

<400> SEQUENCE: 16
```

| Ala | Ile | Gln | Leu | Thr | Gln | Ser | Pro | Ser | Ser | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Gly | Ile | Ser | Ser | Val |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Ser | Gly | Lys | Ala | Pro | Lys | Phe | Leu | Ile |
|---|---|---|---|---|---|---|---|---|---|---|---|---|---|---|---|
| | | 35 | | | | | 40 | | | | | 45 | | | |

| Tyr | Asp | Ala | Ser | Ser | Leu | Glu | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Gln | Gln | Phe | Asn | Ser | Tyr | Pro | Pro |
|---|---|---|---|---|---|---|---|---|---|---|---|---|---|---|---|
| | | | | 85 | | | | | 90 | | | | | 95 | |

| Thr | Phe | Gly | Gln | Gly | Thr | Lys | Leu | Glu | Ile | Lys |
|---|---|---|---|---|---|---|---|---|---|---|
| | | | 100 | | | | | 105 | | |

```
<210> SEQ ID NO 17
<211> LENGTH: 8
<212> TYPE: PRT
<213> ORGANISM: Homo sapiens

<400> SEQUENCE: 17
```

| Gly | Phe | Thr | Phe | Ser | Ser | Tyr | Gly |
|---|---|---|---|---|---|---|---|
| 1 | | | | 5 | | | |

-continued

```
<210> SEQ ID NO 18
<211> LENGTH: 5
<212> TYPE: PRT
<213> ORGANISM: Homo sapiens

<400> SEQUENCE: 18

Val Ala Val Ile Leu
 1               5

<210> SEQ ID NO 19
<211> LENGTH: 12
<212> TYPE: PRT
<213> ORGANISM: Homo sapiens

<400> SEQUENCE: 19

Ala Arg Ile Ala Pro Ala Gly Ser Ala Phe Asp Tyr
 1               5                  10

<210> SEQ ID NO 20
<211> LENGTH: 6
<212> TYPE: PRT
<213> ORGANISM: Homo sapiens

<400> SEQUENCE: 20

Gln Gly Ile Ser Ser Val
 1               5

<210> SEQ ID NO 21
<211> LENGTH: 3
<212> TYPE: PRT
<213> ORGANISM: Homo sapiens

<400> SEQUENCE: 21

Asp Ala Ser
 1

<210> SEQ ID NO 22
<211> LENGTH: 9
<212> TYPE: PRT
<213> ORGANISM: Homo sapiens

<400> SEQUENCE: 22

Gln Gln Phe Asn Ser Tyr Pro Pro Thr
 1               5

<210> SEQ ID NO 23
<211> LENGTH: 708
<212> TYPE: DNA
<213> ORGANISM: Homo sapiens
<220> FEATURE:
<221> NAME/KEY: CDS
<222> LOCATION: (1)...(708)

<400> SEQUENCE: 23 atg gac atg atg gtc ccc gct cag ctc ctg ggg ctt ctg ctg ctc tgg      48
Met Asp Met Met Val Pro Ala Gln Leu Leu Gly Leu Leu Leu Leu Trp
 1               5                  10                  15 ctc cca ggt gcc aga tgt gcc atc cag ttg acc cag tct cca tcc tcc      96
Leu Pro Gly Ala Arg Cys Ala Ile Gln Leu Thr Gln Ser Pro Ser Ser
                20                  25                  30 ctg tct gca tct gta gga gac aga gtc acc atc act tgc cgg gca agt     144
Leu Ser Ala Ser Val Gly Asp Arg Val Thr Ile Thr Cys Arg Ala Ser
             35                  40                  45 cag ggc att agc agt gtt tta gcc tgg tat cag cag aaa tca ggg aaa     192
```

-continued

```
                Gln Gly Ile Ser Ser Val Leu Ala Trp Tyr Gln Gln Lys Ser Gly Lys
                     50                  55                  60 gct cct aag ttc ctg atc tat gat gcc tcc agt ttg gaa agt ggg gtc       240
Ala Pro Lys Phe Leu Ile Tyr Asp Ala Ser Ser Leu Glu Ser Gly Val
 65                  70                  75                  80 cca tca agg ttc agc ggc agt gga tct ggg aca gat ttc act ctc acc       288
Pro Ser Arg Phe Ser Gly Ser Gly Ser Gly Thr Asp Phe Thr Leu Thr
                     85                  90                  95 atc agc agc ctg cag cct gaa gat ttt gca act tat tac tgt caa cag       336
Ile Ser Ser Leu Gln Pro Glu Asp Phe Ala Thr Tyr Tyr Cys Gln Gln
                 100                 105                 110 ttt aat agt tac cct ccc act ttt ggc cag ggg acc aag ctg gag atc       384
Phe Asn Ser Tyr Pro Pro Thr Phe Gly Gln Gly Thr Lys Leu Glu Ile
             115                 120                 125 aaa cgt acg gtg gct gca cca tct gtc ttc atc ttc ccg cca tct gat       432
Lys Arg Thr Val Ala Ala Pro Ser Val Phe Ile Phe Pro Pro Ser Asp
130                 135                 140 gag cag ttg aaa tct gga act gcc tct gtt gtg tgc ctg ctg aat aac       480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc       528
Phe Tyr Pro Arg Glu Ala Lys Val Gln Trp Lys Val Asp Asn Ala Leu
                 165                 170                 175 caa tcg ggt aac tcc cag gag agt gtc aca gag cag gac agc aag gac       576
Gln Ser Gly Asn Ser Gln Glu Ser Val Thr Glu Gln Asp Ser Lys Asp
             180                 185                 190 agc acc tac agc ctc agc agc acc ctg acg ctg agc aaa gca gac tac       624
Ser Thr Tyr Ser Leu Ser Ser Thr Leu Thr Leu Ser Lys Ala Asp Tyr
         195                 200                 205 gag aaa cac aaa gtc tac gcc tgc gaa gtc acc cat cag ggc ctg agc       672
Glu Lys His Lys Val Tyr Ala Cys Glu Val Thr His Gln Gly Leu Ser
     210                 215                 220 tcg ccc gtc aca aag agc ttc aac agg gga gag tgt                       708
Ser Pro Val Thr Lys Ser Phe Asn Arg Gly Glu Cys
225                 230                 235

<210> SEQ ID NO 24
<211> LENGTH: 236
<212> TYPE: PRT
<213> ORGANISM: Homo sapiens

<400> SEQUENCE: 24

Met Asp Met Met Val Pro Ala Gln Leu Leu Gly Leu Leu Leu Leu Trp
 1               5                  10                  15

Leu Pro Gly Ala Arg Cys Ala Ile Gln Leu Thr Gln Ser Pro Ser Ser
             20                  25                  30

Leu Ser Ala Ser Val Gly Asp Arg Val Thr Ile Thr Cys Arg Ala Ser
         35                  40                  45

Gln Gly Ile Ser Ser Val Leu Ala Trp Tyr Gln Gln Lys Ser Gly Lys
     50                  55                  60

Ala Pro Lys Phe Leu Ile Tyr Asp Ala Ser Ser Leu Glu Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
             100                 105                 110

Phe Asn Ser Tyr Pro Pro Thr Phe Gly Gln Gly Thr Lys Leu Glu Ile
         115                 120                 125
```

```
Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 25
<211> LENGTH: 1404
<212> TYPE: DNA
<213> ORGANISM: Homo sapiens
<220> FEATURE:
<221> NAME/KEY: CDS
<222> LOCATION: (1)...(1404)

<400> SEQUENCE: 25 atg gag ttt ggg ctg agc tgg gtt ttc ctc gtt gct ctt tta aga ggt      48
Met Glu Phe Gly Leu Ser Trp Val Phe Leu Val Ala Leu Leu Arg Gly
 1               5                  10                  15 gtc cag tgt cag gtg cag ctg gtg gag tct ggg gga ggc gtg gtc cag      96
Val Gln Cys Gln Val Gln Leu Val Glu Ser Gly Gly Gly Val Val Gln
             20                  25                  30 cct ggg agg tcc ctg aga ctc tcc tgt gca gcg tct gga ttc acc ttc     144
Pro Gly Arg Ser Leu Arg Leu Ser Cys Ala Ala Ser Gly Phe Thr Phe
         35                  40                  45 agt agc tat ggc atg cac tgg gtc cgc cag gct cca ggc aag ggg ctg     192
Ser Ser Tyr Gly Met His Trp Val Arg Gln Ala Pro Gly Lys Gly Leu
     50                  55                  60 gag tgg gtg gca gtt ata tta tat gat gga agt aat aaa tac cat gca     240
Glu Trp Val Ala Val Ile Leu Tyr Asp Gly Ser Asn Lys Tyr His Ala
 65                  70                  75                  80 gac tcc gtg aag ggc cga ttc acc atc tcc aga gac aat tcc aag aac     288
Asp Ser Val Lys Gly Arg Phe Thr Ile Ser Arg Asp Asn Ser Lys Asn
                 85                  90                  95 acg ctg tat ctg caa atg aac agc ctg aga gcc gag gac acg gct gtg     336
Thr Leu Tyr Leu Gln Met Asn Ser Leu Arg Ala Glu Asp Thr Ala Val
            100                 105                 110 tat tac tgt gcg cga ata gca cca gct ggt tcg gcc ttt gac tac tgg     384
Tyr Tyr Cys Ala Arg Ile Ala Pro Ala Gly Ser Ala Phe Asp Tyr Trp
        115                 120                 125 ggc cag gga acc ctg gtc acc gtc tcc tcg gcc tcc acc aag ggc cca     432
Gly Gln Gly Thr Leu Val Thr Val Ser Ser Ala Ser Thr Lys Gly Pro
    130                 135                 140 tcg gtc ttc ccc ctg gca ccc tcc tcc aag agc acc tct ggg ggc aca     480
Ser Val Phe Pro Leu Ala Pro Ser Ser Lys Ser Thr Ser Gly Gly Thr
145                 150                 155                 160 gcg gcc ctg ggc tgc ctg gtc aag gac tac ttc ccc gaa ccg gtg acg     528
Ala Ala Leu Gly Cys Leu Val Lys Asp Tyr Phe Pro Glu Pro Val Thr
                165                 170                 175 gtg tcg tgg aac tca ggc gcc ctg acc agc ggc gtg cac acc ttc ccg     576
Val Ser Trp Asn Ser Gly Ala Leu Thr Ser Gly Val His Thr Phe Pro
            180                 185                 190
```

```
gct gtc cta cag tcc tca gga ctc tac tcc ctc agc agc gtg gtg acc      624
Ala Val Leu Gln Ser Ser Gly Leu Tyr Ser Leu Ser Ser Val Val Thr
        195                 200                 205 gtg ccc tcc agc agc ttg ggc acc cag acc tac atc tgc aac gtg aat      672
Val Pro Ser Ser Ser Leu Gly Thr Gln Thr Tyr Ile Cys Asn Val Asn
    210                 215                 220 cac aag ccc agc aac acc aag gtg gac aag aga gtt gag ccc aaa tct      720
His Lys Pro Ser Asn Thr Lys Val Asp Lys Arg Val Glu Pro Lys Ser
225                 230                 235                 240 tgt gac aaa act cac aca tgc cca ccg tgc cca gca cct gaa ctc ctg      768
Cys Asp Lys Thr His Thr Cys Pro Pro Cys Pro Ala Pro Glu Leu Leu
                245                 250                 255 ggg gga ccg tca gtc ttc ctc ttc ccc cca aaa ccc aag gac acc ctc      816
Gly Gly Pro Ser Val Phe Leu Phe Pro Pro Lys Pro Lys Asp Thr Leu
            260                 265                 270 atg atc tcc cgg acc cct gag gtc aca tgc gtg gtg gtg gac gtg agc      864
Met Ile Ser Arg Thr Pro Glu Val Thr Cys Val Val Val Asp Val Ser
        275                 280                 285 cac gaa gac cct gag gtc aag ttc aac tgg tac gtg gac ggc gtg gag      912
His Glu Asp Pro Glu Val Lys Phe Asn Trp Tyr Val Asp Gly Val Glu
    290                 295                 300 gtg cat aat gcc aag aca aag ccg cgg gag gag cag tac aac agc acg      960
Val His Asn Ala Lys Thr Lys Pro Arg Glu Glu Gln Tyr Asn Ser Thr
305                 310                 315                 320 tac cgt gtg gtc agc gtc ctc acc gtc ctg cac cag gac tgg ctg aat     1008
Tyr Arg Val Val Ser Val Leu Thr Val Leu His Gln Asp Trp Leu Asn
                325                 330                 335 ggc aag gag tac aag tgc aag gtc tcc aac aaa gcc ctc cca gcc ccc     1056
Gly Lys Glu Tyr Lys Cys Lys Val Ser Asn Lys Ala Leu Pro Ala Pro
            340                 345                 350 atc gag aaa acc atc tcc aaa gcc aaa ggg cag ccc cga gaa cca cag     1104
Ile Glu Lys Thr Ile Ser Lys Ala Lys Gly Gln Pro Arg Glu Pro Gln
        355                 360                 365 gtg tac acc ctg ccc cca tcc cgg gag gag atg acc aag aac cag gtc     1152
Val Tyr Thr Leu Pro Pro Ser Arg Glu Glu Met Thr Lys Asn Gln Val
    370                 375                 380 agc ctg acc tgc ctg gtc aaa ggc ttc tat ccc agc gac atc gcc gtg     1200
Ser Leu Thr Cys Leu Val Lys Gly Phe Tyr Pro Ser Asp Ile Ala Val
385                 390                 395                 400 gag tgg gag agc aat ggg cag ccg gag aac aac tac aag acc acg cct     1248
Glu Trp Glu Ser Asn Gly Gln Pro Glu Asn Asn Tyr Lys Thr Thr Pro
                405                 410                 415 ccc gtg ctg gac tcc gac ggc tcc ttc ttc ctc tat agc aag ctc acc     1296
Pro Val Leu Asp Ser Asp Gly Ser Phe Phe Leu Tyr Ser Lys Leu Thr
            420                 425                 430 gtg gac aag agc agg tgg cag cag ggg aac gtc ttc tca tgc tcc gtg     1344
Val Asp Lys Ser Arg Trp Gln Gln Gly Asn Val Phe Ser Cys Ser Val
        435                 440                 445 atg cat gag gct ctg cac aac cac tac acg cag aag agc ctc tcc ctg     1392
Met His Glu Ala Leu His Asn His Tyr Thr Gln Lys Ser Leu Ser Leu
    450                 455                 460 tct ccg ggt aaa                                                     1404
Ser Pro Gly Lys
465

<210> SEQ ID NO 26
<211> LENGTH: 468
<212> TYPE: PRT
<213> ORGANISM: Homo sapiens
```

-continued

```
<400> SEQUENCE: 26

Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Leu Tyr Asp Gly Ser Asn Lys Tyr His Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ile Ala Pro Ala Gly Ser Ala Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415
```

```
Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 27
<211> LENGTH: 143
<212> TYPE: PRT
<213> ORGANISM: Homo sapiens

<400> SEQUENCE: 27

Met Glu Phe Gly Leu Asn Trp Val Phe Leu Val Ala Leu Leu Arg Gly
  1               5                  10                  15

Val Gln Gln Val Gln Leu Val Glu Ser Gly Gly Val Val Gln Pro
             20                  25                  30

Gly Arg Ser Leu Arg Leu Ser Cys Ala Ala Ser Gly Phe Thr Phe Ser
             35                  40                  45

Ser Tyr Gly Met His Trp Val Arg Gln Ala Pro Gly Lys Gly Leu Glu
         50                  55                  60

Trp Val Ala Val Ile Leu Tyr Asp Gly Ser Asn Lys Tyr His Ala Asp
 65                  70                  75                  80

Ser Val Lys Gly Arg Phe Thr Ile Ser Arg Asp Asn Ser Lys Asn Thr
                 85                  90                  95

Leu Tyr Leu Gln Met Asn Ser Leu Arg Ala Glu Asp Thr Ala Val Tyr
            100                 105                 110

Tyr Cys Ala Arg Ile Ala Pro Ala Gly Ser Ala Phe Asp Tyr Trp Gly
        115                 120                 125

Gln Gly Thr Leu Val Thr Val Ser Ser Ala Ser Thr Lys Gly Pro
    130                 135                 140

<210> SEQ ID NO 28
<211> LENGTH: 127
<212> TYPE: PRT
<213> ORGANISM: Homo sapiens

<400> SEQUENCE: 28

Met Glu Ala Pro Ala Gln Leu Leu Phe Leu Leu Leu Leu Trp Leu Pro
  1               5                  10                  15

Asp Thr Thr Gly Ala Ile Gln Leu Thr Gln Ser Pro Ser Ser Leu Ser
             20                  25                  30

Ala Ser Val Gly Asp Arg Val Thr Ile Thr Cys Arg Ala Ser Gln Gly
             35                  40                  45

Ile Ser Ser Val Leu Ala Trp Tyr Gln Gln Lys Ser Gly Lys Ala Pro
         50                  55                  60

Lys Phe Leu Ile Tyr Asp Ala Ser Ser Leu Glu Ser Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Thr Tyr Tyr Cys Gln Gln Phe Asn
            100                 105                 110

Ser Tyr Pro Pro Thr Phe Gly Gln Gly Thr Lys Leu Glu Ile Lys
        115                 120                 125
```

```
<210> SEQ ID NO 29
<211> LENGTH: 10
<212> TYPE: PRT
<213> ORGANISM: Homo sapiens
<220> FEATURE:
<221> NAME/KEY: VARIANT
<222> LOCATION: 6
<223> OTHER INFORMATION: Xaa = Thr or Ser
<220> FEATURE:
<221> NAME/KEY: VARIANT
<222> LOCATION: 8
<223> OTHER INFORMATION: Xaa = Ala or Gly

<400> SEQUENCE: 29

Gly Phe Thr Phe Ser Xaa Tyr Xaa Met His
 1               5                  10

<210> SEQ ID NO 30
<211> LENGTH: 19
<212> TYPE: PRT
<213> ORGANISM: Homo sapiens
<220> FEATURE:
<221> NAME/KEY: VARIANT
<222> LOCATION: 4
<223> OTHER INFORMATION: Xaa = Val or Ile
<220> FEATURE:
<221> NAME/KEY: VARIANT
<222> LOCATION: 5
<223> OTHER INFORMATION: Xaa = Ser or Leu
<220> FEATURE:
<221> NAME/KEY: VARIANT
<222> LOCATION: 9
<223> OTHER INFORMATION: Xaa = Arg or Ser
<220> FEATURE:
<221> NAME/KEY: VARIANT
<222> LOCATION: 10
<223> OTHER INFORMATION: Xaa = Ile or Asn
<220> FEATURE:
<221> NAME/KEY: VARIANT
<222> LOCATION: 12
<223> OTHER INFORMATION: Xaa = Asp or Tyr
<220> FEATURE:
<221> NAME/KEY: VARIANT
<222> LOCATION: 13
<223> OTHER INFORMATION: Xaa = Tyr or His

<400> SEQUENCE: 30

Val Ala Val Xaa Xaa Tyr Asp Gly Xaa Xaa Lys Xaa Xaa Ala Asp Ser
 1               5                  10                  15

Val Lys Gly

<210> SEQ ID NO 31
<211> LENGTH: 11
<212> TYPE: PRT
<213> ORGANISM: Homo sapiens
<220> FEATURE:
<221> NAME/KEY: VARIANT
<222> LOCATION: 3
<223> OTHER INFORMATION: Xaa = Glu or Ile
<220> FEATURE:
<221> NAME/KEY: VARIANT
<222> LOCATION: 4
<223> OTHER INFORMATION: Xaa = Arg or Ala
<220> FEATURE:
<221> NAME/KEY: VARIANT
<222> LOCATION: 5
<223> OTHER INFORMATION: Xaa = Phe or Pro
<220> FEATURE:
<221> NAME/KEY: VARIANT
<222> LOCATION: 7
<223> OTHER INFORMATION: Xaa = Ala or Ser
<220> FEATURE:
```

```
<221> NAME/KEY: VARIANT
<222> LOCATION: 8
<223> OTHER INFORMATION: Xaa = Tyr or Ser

<400> SEQUENCE: 31

Ala Arg Xaa Xaa Xaa Gly Xaa Xaa Phe Asp Tyr
 1               5                  10

<210> SEQ ID NO 32
<211> LENGTH: 10
<212> TYPE: PRT
<213> ORGANISM: Homo sapiens
<220> FEATURE:
<221> NAME/KEY: VARIANT
<222> LOCATION: 5
<223> OTHER INFORMATION: Xaa = Ser or Gly
<220> FEATURE:
<221> NAME/KEY: VARIANT
<222> LOCATION: 6
<223> OTHER INFORMATION: Xaa = Val or Ile
<220> FEATURE:
<221> NAME/KEY: VARIANT
<222> LOCATION: 9
<223> OTHER INFORMATION: Xaa = Tyr or Val

<400> SEQUENCE: 32

Arg Ala Ser Gln Xaa Xaa Ser Ser Xaa Leu
 1               5                  10

<210> SEQ ID NO 33
<211> LENGTH: 7
<212> TYPE: PRT
<213> ORGANISM: Homo sapiens
<220> FEATURE:
<221> NAME/KEY: VARIANT
<222> LOCATION: 4
<223> OTHER INFORMATION: Xaa = Asn or Ser
<220> FEATURE:
<221> NAME/KEY: VARIANT
<222> LOCATION: 5
<223> OTHER INFORMATION: Xaa = Arg or Leu
<220> FEATURE:
<221> NAME/KEY: VARIANT
<222> LOCATION: 6
<223> OTHER INFORMATION: Xaa = Ala or Glu
<220> FEATURE:
<221> NAME/KEY: VARIANT
<222> LOCATION: 7
<223> OTHER INFORMATION: Xaa = Thr or Ser

<400> SEQUENCE: 33

Asp Ala Ser Xaa Xaa Xaa Xaa
 1               5

<210> SEQ ID NO 34
<211> LENGTH: 8
<212> TYPE: PRT
<213> ORGANISM: Homo sapiens
<220> FEATURE:
<221> NAME/KEY: VARIANT
<222> LOCATION: 4
<223> OTHER INFORMATION: Xaa = Arg or Phe
<220> FEATURE:
<221> NAME/KEY: VARIANT
<222> LOCATION: 6
<223> OTHER INFORMATION: Xaa = Asn or Ser
<220> FEATURE:
<221> NAME/KEY: VARIANT
```

-continued

```
<222> LOCATION: 7
<223> OTHER INFORMATION: Xaa = Trp or Tyr

<400> SEQUENCE: 34

Cys Gln Gln Xaa Asn Xaa Xaa Pro
 1              5
```

HUMAN ANTIBODIES AGAINST RABIES AND USES THEREOF

RELATED INFORMATION

The application claims priority to PCT Application No. PCT/US2006/003644 filed on Feb. 2, 2006, and U.S. Provisional Patent Application No. 60/649,512, filed on Feb. 2, 2005, the entire contents of which are hereby incorporated by reference.

The contents of any patents, patent applications, and references cited throughout this specification are hereby incorporated by reference in their entireties.

BACKGROUND OF THE INVENTION

Rabies is an acute progressive encephalitis caused by infection with an RNA virus of the family Rhabdoviridae (genus lyssavirus). While human rabies fatalities are rare in developed nations (there are usually fewer than 5 deaths in the United States each year), significant numbers of deaths are reported in, for example, India, where 50,000 die of the disease and more than 500,000 are treated. Even in the United States, 15,000 to 40,000 people receive anti-rabies treatment each year. Typically, dogs are the major reservoirs of the disease but other mammals such as raccoon, skunk, bat, and fox are frequent reservoirs. Transmission of the virus from an animal reservoir to human usually occurs by a bite or scratch that penetrates the skin. Since rabies in humans is almost always fatal, even a suspected infection must be treated with an aggressive post-exposure treatment regimen.

The post-exposure treatment of rabies in humans consists of proper wound care, local administration of anti-rabies serum immunoglobulin infiltrated into and around the wound, and administration of multiple doses of rabies vaccine usually over several days and weeks (for a review of prophylaxis against rabies, see, e.g., Rupprecht and Gibbons et al., *N Engl J Med* 351:25 (2004)). Proper wound care can lessen the amount of virus that survives to enter the patient. Infiltration of the area with anti-rabies serum immunoglobulin can bind to the rabies virus and help clear it thereby lessening the viral load (by passive immunization). Administration of multiple does of rabies vaccine (active immunization), usually in the form of a first dose followed by subsequent booster doses, allow for the patient to produce a vigorous active immunity, including humoral and cellular responses. Current sources of anti-rabies serum immunoglobulin are obtained from the blood of vaccinated human donors. Other sources of anti-rabies serum immunoglobulin, for example, equine or murine, are considered unacceptable. Current sources of rabies vaccines are produced in cell lines and chemically inactivated and lyophilized. While these agents, when administered in time, are highly effective, certain obstacles remain.

For example, there are few manufacturers of these anti-rabies agents and they remain relatively expensive, especially in the developing world where they are most needed. In addition, human anti-rabies serum immunoglobulin, because it is harvested from the serum of human donors, must be highly purified to prevent the transmission of any adventitious agents. Moreover, the anti-rabies vaccine requires labor intensive cell culture and extensive inactivation and purification steps. Accordingly, improved immunotherapies for treating and preventing rabies infection are needed.

SUMMARY OF THE INVENTION

The present invention solves the foregoing problems by providing a recombinant fully human anti-rabies monoclonal antibody that specifically binds a broad variety of rabies virus isolates and inhibits the ability of the virus to infect cells.

In one embodiment, this is demonstrated by the antibodies ability to neutralize (i.e., inhibit or block) rabies virus in vitro (e.g., in a RFFIT assay). In another embodiment, this is demonstrated by the antibodies ability to inhibit rabies virus infectivity in vivo in a subject, such as an animal or a human.

Human monoclonal antibodies of the invention can be made efficiently, in virtually unlimited amounts, in highly purified form. Accordingly, the antibodies are suitable for prognosing, diagnosing, and/or treating an individual exposed or suspected of having been exposed to rabies. The antibodies of the invention are particularly advantageous for rabies post exposure prophylaxis (PEP) as they eliminate the need for a donor source of human anti-rabies serum immunoglobulin. The antibodies can be produced using a variety of techniques for making human antibodies known in the art. For example, as exemplified herein, the antibodies can be generated in transgenic animals expressing human immunoglobulin gene segments, e.g., transgenic mice comprising a human Ig locus. Moreover, the antibodies can be administered alone or in combination, e.g., with an anti-rabies virus vaccine or other antibodies, to increase survival rates of subjects (e.g., animals and humans) infected with rabies virus.

Accordingly, the invention provides several advantages that include, but are not limited to, the following:

a fully human recombinant anti-rabies antibody for prognosing, diagnosing, and/or treating rabies virus or conducting rabies virus post exposure prophylaxis (PEP) in a subject, e.g., protect from or inhibit rabies virus-mediated morbidity or mortality in a subject;

a composition (e.g., pharmaceutical) and/or a kit comprising one or more fully human recombinant anti-rabies antibodies that can be used alone or in combination with commercially available vaccines to treat rabies infection and/or to conduct PEP in a subject; and an improved method of passive immunotherapy for treating a subject infected with rabies virus (e.g., in need of rabies virus post exposure prophylaxis (PEP)) which can be used alone or in combination with active immunotherapy (rabies vaccine).

In one embodiment, the human monoclonal antibodies or antigen binding portions thereof of the invention specifically bind to rabies virus G glycoprotein. Particular antibodies or antigen binding portions thereof specifically bind to an epitope within the N-terminal half of rabies virus G glycoprotein. Other particular antibodies or antigen binding portions thereof specifically bind to an epitope within the C-terminal domain of rabies virus. Such epitopes can reside, for example, within amino acids 1-50, 50-100, 100-150, 150-200, 200-250, 250-300, 300-350, 350-400, 400-450, 450-500, 500-524 of rabies virus G glycoprotein, or any interval, portion or range thereof. In one embodiment, the antibodies or antigen binding portions thereof specifically bind to an epitope within the N-terminal half of rabies virus G glycoprotein, i.e., between about amino acid residues 19-422. In another embodiment, the epitope of the rabies G glycoprotein comprises amino acid residues 336-442. In one embodiment, the rabies G glycoprotein comprises amino acid residue 336 as well as alterations thereof, such as substitutions or deletions.

In a related embodiment, the rabies G glycoprotein epitope comprises a linear epitope, conformational epitope, discontinuous epitope, or combinations of such epitopes.

In another related embodiment, the rabies G glycoprotein epitope consists of antigenic site I, antigenic site II, antigenic site III, antigenic site minor A, or combinations of such antigenic sites, for example, antigenic site III and minor site A.

In other embodiments, the human monoclonal antibodies or antigen binding portions thereof can be characterized as specifically binding to rabies virus with a $K_D$ of less than about $10 \times 10^{-6}$ M. In a particular embodiment, the antibody or antigen binding portion thereof specifically binds to rabies virus (e.g., a rabies virus G glycoprotein) with a $K_D$ of at least about $10 \times 10^{-7}$ M, at least about $10 \times 10^{-8}$ M, at least about $10 \times 10^{-9}$ M, at least about $10 \times 10^{-10}$ M, at least about $10 \times 10^{-11}$ M, or at least about $10 \times 10^{-12}$ M or a $K_D$ even more favorable.

In various other embodiments, the antibodies or antigen binding portions thereof include a variable heavy chain region comprising an amino acid sequence at least 80%, 85%, 90%, 95%, 98%, 99% or more identical to a variable heavy chain region amino acid sequence of the antibody produced by clone 17C7 (SEQ ID NO: 1), 6G11 (SEQ ID NO: 15), 5G5, 2B10, or 1E5.

In other embodiments, the antibodies or antigen binding portions thereof include a variable light chain region comprising an amino acid sequence at least 80%, 85%, 90%, 95%, 98%, 99% or more identical to a variable light chain region amino acid sequence of the antibody produced by clone 17C7 (SEQ ID NO: 2), 6G11 (SEQ ID NO: 16), 5G5, 2B10, or 1E5.

In still other embodiments, the antibodies or antigen binding portions thereof include both a variable heavy chain region comprising an amino acid sequence at least 80%, 85%, 90%, 95%, 98%, 99% or more identical to a variable heavy chain region amino acid sequence of the antibody produced by clone 17C7 (SEQ ID NO: 1), 6G11 (SEQ ID NO: 15), 5G5, 2B10, or 1E5), and a variable light chain region comprising an amino acid sequence at least 80%, 85%, 90%, 95%, 98%, 99%, or more identical to a variable light chain amino acid sequence of clone 17C7 (SEQ ID NO: 2), 6G11 (SEQ ID NO: 16), 5G5, 2B10, or 1E5.

In certain other embodiments, the antibodies or antigen binding portions thereof specifically bind to an epitope that overlaps with an epitope bound by an antibody produced by clone 17C7, 6G11, 5G5, 2B10, or 1E5 and/or competes for binding to a rabies virus, or portion thereof with an antibody produced by clone 17C7, 6G11, 5G5, 2B10, or 1E5.

The variable heavy and light chain regions of the antibodies or antigen binding portions thereof typically include one or more complementarity determining regions (CDRs). These include the CDR1, CDR2, and CDR3 regions. In particular embodiments, the variable heavy chain CDRs are at least 80%, 85%, 90%, 95%, or 99%, or more identical to a CDR of the antibody produced by clone 17C7 (SEQ ID NOs: 3, 4, 5), 6G11 (SEQ ID NOs: 17, 18, 19), 5G5, 2B10, or 1E5 (also shown in Table 1). In other particular embodiments, variable light chain CDRs are at least 80%, 85%, 90%, 95%, or 99%, or more identical to a CDR of a variable light chain region of the antibody produced by clone 17C7 (SEQ ID NOs: 6, 7, 8), 6G11 (SEQ ID NOs: 20, 21, 22), 5G5, 2B10, or 1E5 (also shown in Table 2).

Accordingly, particular antibodies or fragments of the invention comprise a variable heavy chain region that includes one or more complementarity determining regions (CDRs) that are at least 80%, 85%, 90%, 95%, or 99%, or more identical to a CDR of a variable heavy chain region of the antibody produced by clone 17C7 (SEQ ID NOs: 3, 4, 5), 6G11 (SEQ ID NOs: 17, 18, 19), 5G5, 2B10, or 1E5 and a variable light chain region that includes one or more CDRs that are at least 80%, 85%, 90%, 95%, 99%, or more identical to a CDR of a variable light chain region of the antibody produced by clone 17C7 (SEQ ID NOs: 6, 7, 8), 6G11 (SEQ ID NOs: 20, 21, 22), 5G5, 2B10, or 1E5

The variable heavy chain region of the antibodies or antigen binding portions thereof can also include all three CDRs that are at least 80%, 85%, 90%, 95%, or 99%, or more identical to the CDRs of the variable heavy chain region of the antibody produced by clone 17C7 (SEQ ID NOs: 3, 4, 5), 6G11 (SEQ ID NOs: 17, 18, 19), 5G5, 2B10, or 1E5 and/or all three CDRs that are at least 80%, 85%, 90%, 95%, 99%, or more identical to the CDRs of the variable light chain region of the antibody produced by clone 17C7 (SEQ ID NOs: 6, 7, 8), 6G11 (SEQ ID NOs: 20, 21, 22), 5G5, 2B10, or 1E5.

In another embodiment of the invention, the human antibodies or antigen binding portions thereof (a) include a heavy chain variable region that is encoded by or derived from (i.e., is the product of) a human VH 3-30-3 or VH 3-33 gene; and/or (b) include a light chain variable region that is encoded by or derived from a human Vκ gene selected from the group consisting of Vκ L6, Vκ L11, Vκ L13, Vκ L15, or Vκ L19.

Human monoclonal antibodies of the present invention include full-length antibodies, for example, that include an effector domain, (e.g., an Fc domain), as well as antibody portions or fragments, such as single-chain antibodies and Fab fragments. The antibodies can also be linked to a variety of therapeutic agents (e.g., antiviral agents or toxins) and/or a label.

In another aspect, the invention features isolated polypeptides that include an antigen binding portion of an antibody produced by hybridoma clone 17C7, 6G11, 5G5, 2B10, or 1E5 (also referred to herein as "17C7", "6G11", "5G5", "2B10", and "1E5").

In another aspect, the invention features isolated nucleic acids including a sequence encoding a antibody heavy chain variable region which is at least 75%, 80%, 85%, 90%, 95%, 99%, or more identical to SEQ ID NO: 13 or 23. The invention also features isolated nucleic acids that include a sequence encoding an antibody light chain variable region which is at least 75%, 80%, 85%, 90%, 95%, 99%, or more identical to SEQ ID NO: 14 or 24. The invention also features expression vectors including any of the foregoing nucleic acids either alone or in combination (e.g., expressed from one or more vectors), as well as host cells comprising such expression vectors.

Suitable host cells for expressing antibodies of the invention include a variety of eukaryotic cells, e.g., yeast cells, mammalian cells, e.g., Chinese hamster ovary (CHO) cells, NS0 cells, myeloma cells, or plant cells.

In another aspect, the invention features compositions and kits that include one or more isolated human monoclonal antibodies or antigen binding portions thereof as described herein that specifically bind to rabies virus and inhibit the ability of the virus to infect mammalian cells. The composition or kit can further include one or more antibodies (e.g., human monoclonal or polyclonal antibodies) or antigen-binding portions thereof that specifically bind to rabies virus. In one embodiment, the polyclonal antibody or antigen binding portion thereof specifically binds to rabies virus G glycoprotein. In a particular embodiment, the composition or kit includes both (a) an isolated human monoclonal antibody that specifically binds to a first rabies virus isolate; and (b) an isolated human monoclonal antibody that specifically binds to a second rabies virus isolate.

The invention also features methods of treating rabies virus disease in a subject by administering to the subject an isolated human monoclonal antibody or antigen binding portion thereof as described herein (i.e., that specifically binds to rabies virus) in an amount effective to inhibit rabies virus disease, e.g., rabies virus-mediated symptoms or morbidity.

Human monoclonal antibodies or portions thereof (and compositions comprising the antibodies or portions thereof) of the invention can be administered in a variety of suitable fashions, e.g., intravenously (IV), subcutaneously (SC), and preferably, intramuscularly (IM) to the subject. The antibody or antigen-binding portion thereof can be administered alone or in combination with another therapeutic agent, e.g., a second human monoclonal antibody or antigen binding portion thereof. In one example, the second human monoclonal antibody or antigen binding portion thereof specifically binds to a second rabies virus isolate that differs from the isolate bound to the first antibody. In another example, the antibody is administered together with another agent, for example, an antiviral agent. In another example, the antibody is administered together with a polyclonal gamma-globulin (e.g., human gamma-globulin). In another example, the antibody is administered before, after, or contemporaneously with a rabies virus vaccine.

In another aspect, the invention features methods for making an antibody or antigen binding portion thereof that specifically binds to a rabies virus. In one embodiment, the method involves immunizing a transgenic non-human animal having a genome comprising a human heavy chain transgene and a human light chain transgene with a composition that includes a rabies virus, e.g., live or inactivated virus and isolating an antibody, antibody producing cell, or antibody encoding nucleic acid from the animal. The rabies virus can be inactivated, for example, by chemical treatment and/or lyophilization. The method can further include evaluating binding of the antibody to the rabies virus or rabies virus G glycoprotein.

The invention also features methods for making the antibodies or antigen binding portions thereof by expressing nucleic acids encoding human antibodies in a host cell (e.g., nucleic acids encoding the antigen binding region portion of an antibody). In yet another aspect, the invention features a hybridoma or transfectoma including the aforementioned nucleic acids.

The invention also features a method for making a hybridoma that expresses an antibody that specifically binds to a rabies virus by immunizing a transgenic non-human animal having a genome that includes a human heavy chain transgene and a human light chain transgene, with a composition that includes the rabies virus or rabies virus G glycoprotein; isolating splenocytes from the animal; generating hybridomas from the splenocytes; and selecting a hybridoma that produces an antibody that specifically binds to rabies virus or rabies virus protein thereof.

Treatment of humans with human monoclonal antibodies offers several advantages. For example, the antibodies are likely to be less immunogenic in humans than non-human antibodies. The therapy is also rapid because rabies virus inactivation can occur as soon as the antibody reaches sites of infection and directly neutralizes the disease-causing rabies virus. Human antibodies also localize to appropriate sites in humans more efficiently than non-human antibodies. Furthermore, the treatment is specific for rabies virus, and is recombinant and highly purified and, unlike traditional therapies, avoids the potential of being contaminated with adventitious agents.

Other features and advantages of the invention will be apparent from the following detailed description, and from the claims.

BRIEF DESCRIPTION OF THE DRAWINGS

FIG. 1 shows the amino acid sequence of the heavy and light chain variable region of a recombinant, anti-rabies human antibody (i.e., clone 17C7). These sequences correspond to SEQ ID NOs: 1 and 2, respectively. The complementarity determining regions (CDRs) for each chain are indicated, corresponding to SEQ ID NOs: 3, 4, and 5 (of the heavy chain) and 6, 7, and 8 (of the light chain).

FIG. 2 shows the amino acid sequence of the heavy and light chain variable region of a recombinant, anti-rabies human antibody (i.e., clone 6G11). These sequences correspond to SEQ ID NOs: 15 and 16, respectively. The complementarity determining regions (CDRs) for each chain are indicated, corresponding to SEQ ID NOs: 17, 18, and 19 (of the heavy chain) and 20, 21, and 22 (of the light chain).

FIG. 3 is a schematic representation of the rabies virus G recombinant glycoprotein indicating fragments that were analyzed for epitope mapping studies. Human antibody 17C7 was determined to bind epitope(s) within amino acid residues 19-422 as determined by immunoprecipitation and immunoblot.

FIG. 7 shows that HuMab 17C7 recognizes N336K and N336D mutant ERA glycoproteins (A) by ELISA and by immunoblot (B).

FIG. 9 shows the consequences of various mutations to the ERA G protein (A-B) regarding 17C7 binding thereto.

DETAILED DESCRIPTION OF THE INVENTION

Figure 4:
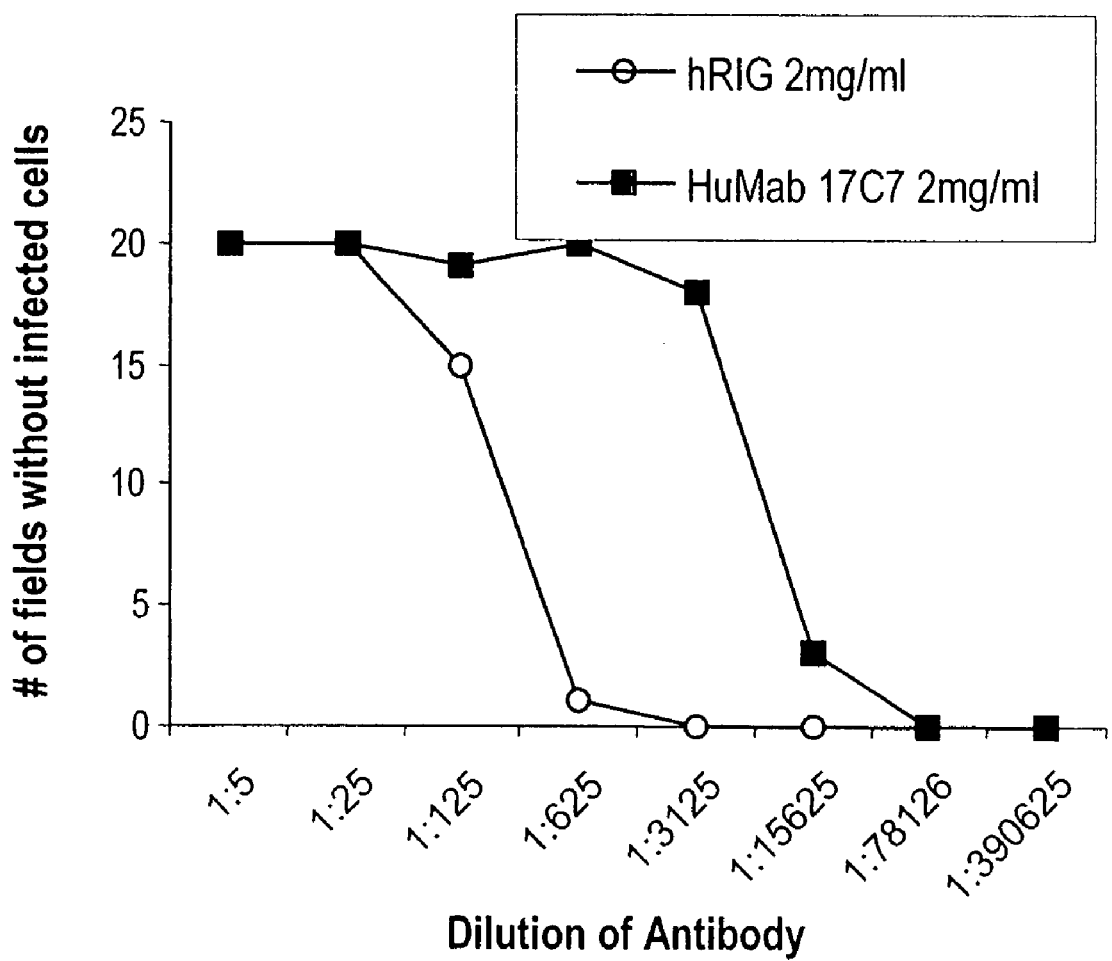
FIG. 4 shows HuMab 17C7 neutralizes rabies virus as determined by RFFIT when diluted serially from 1:5 to 1:390625 as compared to human serum (hRIG).

In order to provide a clear understanding of the specification and claims, the following definitions are conveniently provided below.

Definitions

As used herein, the term "rabies virus" refers to the virion or portion thereof, for example protein portion, such as rabies virus G glycoprotein that is encoded by the RNA of rabies virus.

The term "anti-rabies virus antibody" is an antibody that interacts with (e.g., binds to) a rabies virus or a protein, carbohydrate, lipid, or other component produced by or associated with rabies virus. A "rabies virus G glycoprotein antibody" is an antibody that binds a G glycoprotein of rabies virus or a fragment thereof. An anti-rabies virus or G glycoprotein antibody may bind to an epitope, e.g., a conformational or a linear epitope, or to a portion or fragment of the virus or component thereof.

The term "human antibody" is an antibody that has variable and constant regions derived from human germline immunoglobulin sequences. The human antibodies described herein may include amino acid residues not encoded by human germline immunoglobulin sequences (e.g., mutations introduced by random or site-specific mutagenesis in vitro or by somatic mutation in vivo).

An anti-rabies virus antibody, or antigen-binding portion thereof, can be administered alone or in combination with a second agent. The subject can be a patient infected or suspected to be infected with rabies virus or having a symptom of rabies virus-mediated disease (e.g., an neuropathology, encephalomyelitis, or anti-rabies immunoglobulin serum titer). The treatment can be used to cure, heal, alleviate, relieve, alter, remedy, ameliorate, palliate, improve, or affect the infection and the disease associated with the infection, the symptoms of the disease, or a predisposition toward the disease. For the clinical management of rabies virus infection, "treatment" is frequently understood to mean the prophylaxis or prevention of a productive infection before the onset of illness.

An amount of an anti-rabies virus antibody effective to treat a rabies virus infection, or a "therapeutically effective amount" is an amount of the antibody that is effective, upon single or multiple dose administration to a subject, in inhibiting rabies virus infection, disease, or sequelae thereof, in a subject. A therapeutically effective amount of the antibody or antibody fragment may vary according to factors such as the disease state, wound site, rabies virus strain or isolate, animal vector of rabies virus, age, sex, and weight of the individual, and the ability of the antibody or antibody portion to elicit a desired response in the individual. A therapeutically effective amount is also one in which any toxic or detrimental effects of the antibody or antibody portion is outweighed by the therapeutically beneficial effects. The ability of an antibody to inhibit a measurable parameter can be evaluated in an animal model system predictive of efficacy in humans. For example, the ability of an anti-rabies virus antibody to protect hamsters from lethal challenge with rabies virus can predict efficacy in humans, as described in the Examples. Alternatively, this property of an antibody or antibody composition can be evaluated by examining the ability of the compound to modulate rabies virus/cell interactions, e.g., binding, infection, virulence, and the like, by in vitro by assays known to the skilled practitioner. In vitro assays include binding assays, such as ELISA, and neutralization assays.

An amount of an anti-rabies virus antibody effective to prevent a disorder, or a "prophylactically effective amount," of the antibody is an amount that is effective, upon single- or multiple-dose administration to the subject, in preventing or delaying the occurrence of the onset or recurrence of rabies virus, or inhibiting a symptom thereof. However, if longer time intervals of protection are desired, increased doses or more frequent doses can be administered.

The terms "antagonize", "induce", "inhibit", "potentiate", "elevate", "increase", "decrease", or the like, e.g., which denote quantitative differences between two states, refer to a difference, e.g., a statistically or clinically significant difference, between the two states.

The term "specific binding" or "specifically binds to" refers to the ability of an antibody to bind to a rabies virus, or portion thereof, with an affinity of at least $1 \times 10^{-6}$ M, and/or bind to a rabies virus, or portion thereof, with an affinity that is at least two-fold greater than its affinity for a nonspecific antigen.

An "antibody" is a protein including at least one or two, heavy (H) chain variable regions (abbreviated herein as VH), and at least one or two light (L) chain variable regions (abbreviated herein as VL). The VH and VL regions can be further subdivided into regions of hypervariability, termed "complementarity determining regions" (CDRs), interspersed with regions that are more conserved, termed "framework regions" (FR). The extent of the framework region and CDRs has been precisely defined (see, Kabat, E. A., et al. *Sequences of Proteins of Immunological Interest*, Fifth Edition, U.S. Department of Health and Human Services, NIH Publication No. 91-3242, 1991, and Chothia, C. et al., *J. Mol. Biol.* 196:901-917, 1987, which are incorporated herein by reference). Preferably, each VH and VL is composed of three CDRs and four FRs, arranged from amino-terminus to carboxy-terminus in the following order: FR1, CDR1, FR2, CDR2, FR3, CDR3, FR4.

The VH or VL regions of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta (IgD), epsilon (IgE), and mu (IgM) constant region genes, as well as the myriad immunoglobulin variable region genes. Full-length immunoglobulin "light chains" (about 25 $K_D$ and 214 amino acids) are encoded by a variable region gene at the $NH_2$-terminus (about 110 amino acids) and a kappa or lambda constant region gene at the COOH-terminus. Full-length immunoglobulin "heavy chains" (about 50 $K_D$ and 446 amino acids), are similarly encoded by a variable region gene (about 116 amino acids) and one of the other aforementioned constant region genes, e.g., gamma (encoding about 330 amino acids). The term "immunoglobulin" includes an immunoglobulin having: CDRs from a human or non-human source. The framework of the immunoglobulin can be human, humanized, or non-human, e.g., a murine framework modified to decrease antigenicity in humans, or a synthetic framework, e.g., a consensus sequence. A mature immunoglobulin/antibody variable region is typically devoid of a leader sequence. Immunoglobulins/antibodies can be further distinguished by their constant regions into class (e.g., IgA, IgD, IgE, IgG, or IgM) and subclass or isotype (e.g., IgG1, IgG2, IgG3, or IgG4).

The term "antigen binding portion" of an antibody (or simply "antibody portion," or "portion"), as used herein, refers to a portion of an antibody that specifically binds to a rabies virus or component thereof (e.g., G glycoprotein), e.g., a molecule in which one or more immunoglobulin chains is not full length, but which specifically binds to a rabies virus or component thereof. Examples of binding portions encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; and (vi) an isolated complementarity determining region (CDR) having sufficient framework to specifically bind, e.g., an antigen binding portion of a variable region. An antigen binding portion of a light chain variable region and an antigen binding portion of a heavy chain variable region, e.g., the two domains of the Fv fragment, VL and VH, can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen binding portion" of an antibody. These antibody portions are obtained using conventional techniques known to those with skill in the art, and the portions are screened for utility in the same manner as are intact antibodies.

The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or portions thereof with a single molecular composition.

The term "recombinant" antibody, as used herein, refers to antibodies that are prepared, expressed, created, or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created, or isolated by any other means that involves splicing of human immunoglobulin gene sequences to other DNA sequences. Such recombinant antibodies include humanized, CDR grafted, chimeric, in vitro generated (e.g., by phage display) antibodies, and may optionally include constant regions derived from human germline immunoglobulin sequences.

The term "substantially identical" (or "substantially homologous") refers to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the first antibody.

Calculations of "homology" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 50% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences is determined using the Needleman and Wunsch, *J. Mol. Biol.* 48:444-453, 1970, algorithm which has been incorporated into the GAP program in the GCG software package, using a Blossum 62 scoring matrix with a gap penalty of 12, a gap extend penalty of 4, and a frame shift gap penalty of 5.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. 6.3.1-6.3.6, 1989, which is incorporated herein by reference. Aqueous and nonaqueous methods are described in that reference and either can be used. Specific hybridization conditions referred to herein are as follows: 1) low stringency hybridization conditions: 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions: 6×SSC at about 45° C., followed by one or more washes in 0.2×SSC, 0.1% SDS at 60° C.; 3) high stringency hybridization conditions: 6×SSC at about 45° C., followed by one or more washes in 0.2×SSC, 0.1% SDS at 65° C.; and 4) very high stringency hybridization conditions: 0.5 M sodium phosphate, 7% SDS at 65° C., followed by one or more washes at 0.2×SSC, 1% SDS at 65° C.

It is understood that the antibodies and antigen binding portions thereof described herein may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie et al., *Science,* 247:1306-1310, 1990. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of a polypeptide, such as a binding agent, e.g., an antibody, without substantially altering a biological activity, whereas an "essential" amino acid residue results in such a change.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Overview

Rabies virus is a RNA virus that causes fatal encephalitis in humans. Provided herein are methods and compositions for treatment and prevention of rabies virus infected animals, in particular, human subjects, more particularly, humans in need of post exposure rabies treatment or post exposure prophylaxis (PEP). The compositions include antibodies that recognize proteins and other molecular components (e.g., lipids, carbohydrates, nucleic acids) of rabies virus, including antibodies that recognize the rabies virus G glycoprotein, or portion thereof. In particular, recombinant fully human monoclonal antibodies are provided. In certain embodiments, these human monoclonal antibodies are produced in mice expressing human immunoglobulin gene segments (described below). Combinations of anti-rabies virus antibodies are also provided.

The new methods include administering antibodies (and antigen-binding portions thereof) that bind to rabies virus in a subject to inhibit rabies virus-mediated disease in the subject. For example, human monoclonal anti-rabies virus antibodies described herein can neutralize rabies virus and inhibit end-stage rabies infection and encephalitis. In other examples, combinations of anti-rabies virus antibodies (e.g., anti-rabies virus G glycoprotein monoclonal antibodies) can be administered to inhibit rabies virus-mediated disease. The human monoclonal antibodies can be locally administered (infiltrated) at the wound site of rabies infection and, optionally, followed by administration of an anti-rabies vaccine.

1. Generation of Antibodies

Immunogens

In general, animals are immunized with virus and/or antigens expressed by rabies virus to produce antibodies. For producing anti-rabies virus antibodies, animals are typically immunized with inactivated rabies virus. Rabies virus can be inactivated, e.g., by chemical treatment and/or lyophilization and several rabies virus vaccines are available commercially.

Anti-rabies virus antibodies that bind and neutralize rabies virus can interact with specific epitopes of rabies virus, for example, rabies virus G glycoprotein. For example, an anti-rabies virus G glycoprotein can bind an epitope within a N-terminal region of the rabies virus G glycoprotein, or a C-terminal region, or an internal region of the protein or fragment thereof (see Example 4 and FIG. 5) or a combination thereof. In one example, an antibody that binds and neutralizes rabies virus binds to an epitope, for example, a linear epitope, within amino acids 19-422 of rabies virus G glycoprotein. In another example, an antibody is identified that binds a linear epitope and/or conformational epitope within amino acids 19-422 of rabies virus G glycoprotein. As discussed herein, such epitopes can also be used to identify other antibodies that bind rabies.

Generation of Human Monoclonal Antibodies in HuMAb Mice

Monoclonal antibodies can be produced in a manner not possible with polyclonal antibodies. Polyclonal antisera vary from animal to animal, whereas monoclonal preparations exhibit a uniform antigenic specificity. Murine animal systems are useful to generate monoclonal antibodies, and immunization protocols, techniques for isolating and fusing splenocytes, and methods and reagents for producing hybridomas are well known. Monoclonal antibodies can be produced by a variety of techniques, including conventional monoclonal antibody methodology, e.g., the standard somatic cell hybridization technique of Kohler and Milstein, Nature, 256: 495, 1975. See generally, Harlow, E. and Lane, D. Antibodies: A Laboratory Manual, Cold Spring Harbor Laboratory Press, Cold Spring Harbor, N.Y., 1988.

Although these standard techniques are known, it is desirable to use humanized or human antibodies rather than murine antibodies to treat human subjects, because humans mount an immune response to antibodies from mice and other species. The immune response to murine antibodies is called a human anti-mouse antibody or HAMA response (Schroff, R. et al., Cancer Res., 45, 879-885, 1985) and is a condition that causes serum sickness in humans and results in rapid clearance of the murine antibodies from an individual's circulation. The immune response in humans has been shown to be against both the variable and the constant regions of murine immunoglobulins. Human monoclonal antibodies are safer for administration to humans than antibodies derived from other animals and human polyclonal antibodies.

One useful type of animal in which to generate human monoclonal antibodies is a transgenic mouse that expresses human immunoglobulin genes rather than its own mouse immunoglobulin genes. Such transgenic mice, e.g., "HuMAb™" mice, contain human immunoglobulin gene miniloci that encode unrearranged human heavy ($\mu$ and $\gamma$) and $\kappa$ light chain immunoglobulin sequences, together with targeted mutations that inactivate the endogenous $\mu$ and $\kappa$ chain loci (see e.g., Lonberg, N. et al., Nature 368(6474): 856-859, 1994, and U.S. Pat. No. 5,770,429). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg, N. et al., supra; reviewed in Lonberg, N. Handbook of Experimental Pharmacology 113:49-101, 1994; Lonberg, N. and Huszar, D., Intern. Rev. Immunol., 13: 65-93, 1995, and Harding, F. and Lonberg, N., Ann. N.Y Acad. Sci., 764:536-546, 1995).

The preparation of such transgenic mice is described in further detail in Taylor, L. et al., Nucleic Acids Research, 20:6287-6295, 1992; Chen, J. et al., International Immunology 5: 647-656, 1993; Tuaillon et al., Proc. Natl. Acad. Sci., USA 90:3720-3724, 1993; Choi et al., Nature Genetics, 4:117-123, 1993; Chen, J. et al, EMBO J., 12: 821-830, 1993; Tuaillon et al., J. Immunol., 152:2912-2920, 1994; Taylor, L. et al., International Immunology, 6: 579-591, 1994; and Fishwild, D. et al., Nature Biotechnology, 14: 845-851, 1996. See further, U.S. Pat. No. 5,545,806; U.S. Pat. No. 5,569,825, U.S. Pat. No. 5,625,126, U.S. Pat. No. 5,633,425, U.S. Pat. No. 5,661,016, U.S. Pat. No. 5,770,429, U.S. Pat. No. 5,789, 650, U.S. Pat. No. 5,814,318, U.S. Pat. No. 5,874,299 and U.S. Pat. No. 5,877,397, all by Lonberg and Kay, and PCT Publication Nos. WO 01/14424, WO 98/24884, WO 94/25585, WO 93/1227, and WO 92/03918.

To generate fully human monoclonal antibodies to an antigen, HuMAb mice can be immunized with an immunogen, as described by Lonberg, N. et al. Nature, 368(6474): 856-859, 1994; Fishwild, D. et al., Nature Biotechnology, 14: 845-851, 1996 and WO 98/24884. Preferably, the mice are 6-16 weeks of age upon the first immunization. For example, a purified preparation of inactivated rabies virus can be used to immunize the HuMAb mice intraperitonealy. To generate antibodies against rabies virus proteins, lipids, and/or carbohydrate molecules, mice can be immunized with live, killed or non-viable inactivated and/or lyophilized rabies virus. In another embodiment, a rabies virus G glycoprotein, or one or more fragments thereof, can be used as an immunogen.

HuMAb transgenic mice respond best when initially immunized intraperitoneally (IP) with antigen in complete Freund's adjuvant, followed by IP immunizations every other week (up to a total of 6) with antigen in incomplete Freund's adjuvant. The immune response can be monitored over the course of the immunization protocol with plasma samples being obtained by retroorbital bleeds. The plasma can be screened, for example by ELISA or flow cytometry, and mice with sufficient titers of anti-rabies virus human immunoglobulin can be used for fusions. Mice can be boosted intravenously with antigen 3 days before sacrifice and removal of the spleen. It is expected that multiple fusions for each antigen may need to be performed. Several mice are typically immunized for each antigen.

The mouse splenocytes can be isolated and fused with PEG to a mouse myeloma cell line based upon standard protocols. The resulting hybridomas are then screened for the production of antigen-specific antibodies. For example, single cell suspensions of spleenic lymphocytes from immunized mice are fused to one-sixth the number of P3X63-Ag8.653 nonsecreting mouse myeloma cells (ATCC, CRL 1580) with 50% PEG. Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells are cultured in medium in which the HAT is replaced with HT. Supernatants from individual wells are then screened by ELISA for human anti-rabies virus monoclonal IgM and IgG antibodies. The antibody secreting hybridomas are replated, screened again, and if still positive for human IgG, anti-rabies virus monoclonal antibodies, can be subcloned at least twice by limiting dilution. The stable subclones are then cultured in vitro to generate small amounts of antibody in tissue culture medium for characterization.

In one embodiment, the transgenic animal used to generate human antibodies to the rabies virus contains at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884, the contents of which are hereby expressly incorporated by reference. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human K light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Examples 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

The B cells isolated from such an animal are monospecific with regard to the human heavy and light chains because they contain only a single copy of each gene. Furthermore, they will be monospecific with regard to human or mouse heavy chains because both endogenous mouse heavy chain gene copies are nonfunctional by virtue of the deletion spanning the $J_H$ region introduced as described in Examples 9 and 12 of WO 98/24884. Furthermore, a substantial fraction of the B cells will be monospecific with regards to the human or mouse light chains, because expression of the single copy of the rearranged human kappa light chain gene will allelically and isotypically exclude the rearrangement of the endogenous mouse kappa and lambda chain genes in a significant fraction of B-cells.

In one embodiment, the transgenic mouse will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, e.g., 0.5 to 5 mg/ml, or at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, e.g., about 40 to 80% of the spleen and lymph node B cells will express exclusively human IgG protein.

The repertoire in the transgenic mouse will ideally approximate that shown in a non-transgenic mouse, usually at least about 10% as high, preferably 25 to 50% or more as high. Generally, at least about a thousand different immunoglobulins (ideally IgG), preferably $10^4$ to $10^6$ or more, will be produced, depending primarily on the number of different V, J, and D regions introduced into the mouse genome. Typically, the immunoglobulins will exhibit an affinity for preselected antigens of at least about $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, or greater, e.g., up to $10^{-15}$ M or more.

HuMAb mice can produce B cells that undergo class-switching via intratransgene switch recombination (cis-switching) and express immunoglobulins reactive with the rabies virus. The immunoglobulins can be human sequence antibodies, wherein the heavy and light chain polypeptides are encoded by human transgene sequences, which may include sequences derived by somatic mutation and V region recombinatorial joints, as well as germline-encoded sequences. These human sequence immunoglobulins can be referred to as being substantially identical to a polypeptide sequence encoded by a human VL or VH gene segment and a human JL or JL segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments. Frequently at least 85 percent of the variable regions are encoded by human germline sequences present on the transgene. Often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) that are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

The human sequence antibodies that bind to the rabies virus can result from isotype switching, such that human antibodies comprising a human sequence gamma chain (such as gamma 1, gamma 2, or gamma 3) and a human sequence light chain (such as K) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human sequence antibodies have binding affinities of at least about $1\times10^{-9}$ M, typically at least $5\times10^{-9}$ M, frequently more than $1\times10^{-10}$ M, and sometimes $5\times10^{-10}$ M to $1\times10^{-11}$ M or greater.

Anti-rabies virus antibodies can also be raised in other mammals, including non-transgenic mice, humans, rabbits, and goats.

Anti-Rabies Virus Antibodies

Human monoclonal antibodies that specifically bind to rabies virus include antibodies produced by the clones 17C7, 6G11, 5G5, 2B10, and 1E5 described herein (referred to as, respectively, antibody clones 17C7, 6G11, 5G5, 2B10, and 1E5). Antibodies with variable heavy chain and variable light chain regions that are at least 80% identical to the variable heavy and light chain regions of 17C7, 6G11, 5G5, 2B10, or 1E5 can also bind to rabies virus. In related embodiments, anti-rabies virus antibodies include, for example, complementarity determining regions (CDRs) that are at least 80% identical to the CDRs of the variable heavy chains and/or variable light chains of 17C7, 6G11, 5G5, 2B10, or 1E5. The CDRs of the variable heavy chain regions from these antibody clones are shown in Table 1, below.

TABLE 1

Variable Heavy Chain CDR Amino Acid Sequences

| Ab Clone | Chain | CDR | Amino Acid Sequence | SEQ ID NO: |
|---|---|---|---|---|
| 17C7 | H | CDR1 | TYAMH | 3 |
| 17C7 | H | CDR2 | VVSYDGRTKDYADSVKG | 4 |
| 17C7 | H | CDR3 | ERFSGAYFDY | 5 |
| 6G11 | H | CDR1 | GFTFSSYG | 17 |
| 6G11 | H | CDR2 | VAVIL | 18 |
| 6G11 | H | CDR3 | ARIAPAGSAFDY | 19 |

The CDRs of the variable light chain regions from these clones are shown in Table 2, below.

TABLE 2

Variable Light Chain CDR Amino Acid Sequences

| Clone | Chain | CDR | Amino Acid Sequence | SEQ ID NO: |
|---|---|---|---|---|
| 17C7 | L | CDR1 | RASQSVSSYLA | 6 |
| 17C7 | L | CDR2 | DASNRAT | 7 |
| 17C7 | L | CDR3 | QQRNNWP | 8 |
| 6G11 | L | CDR1 | QGISSV | 20 |
| 6G11 | L | CDR2 | DAS | 21 |
| 6G11 | L | CDR3 | QQFNSYPPT | 22 |

CDRs are the portions of immunoglobulins that determine specificity for a particular antigen. In certain embodiments, CDRs corresponding to the CDRs in Tables 1 and 2 having sequence variations (e.g., conservative substitutions) may bind to rabies virus. For example, CDRs, in which 1, 2, 3, 4, or 5 residues, or less than 20% of total residues in the CDR, are substituted or deleted can be present in an antibody (or antigen binding portion thereof) that binds rabies virus.

Similarly, anti-rabies virus antibodies can have CDRs containing a consensus sequence, as sequence motifs conserved amongst multiple antibodies can be important for binding activity.

For example, the invention provides for the use of one or more CDR regions or derivatives of the disclosed CDRs. Such derivative CDRs are derived from a disclosed CDR or portion thereof and, optionally, altered at one more amino acid positions. Alterations include one or more amino acid additions, deletions, or substitutions as described herein. Exemplary residue positions for altering include those amino acid positions identified as subject to more variance than other amino acid positions, for example, positions subject to somatic mutations as known in the art. Alternatively, such positions can be identified by comparing two or more sequences known to have a desired binding activity and identifying CDR residues that vary and CDR residues that are constant. For example, a comparison of the variable regions of 17C7 and 6G11 heavy and light chains are presented below (Tables 3-4) and the CDR derivative or consensus sequences that can be determined therefrom are shown (Tables 5-6).

TABLE 3

Comparison of Heavy Chain Variable Regions

```
Comparison of:
17c7H                                  -126 aa
6G11H                                  -125 aa
using matrix file: BLOSUM50, gap penalties: -14/-4
87.2% identity in 125 aa overlap; score:    731

10        20        30        40        50        60
QVQLVESGGGVVQPGRSLRLSCAASGFTFSTYAMHWVRQAPGKGLEWVAVVSYDGRTKDY    SEQ ID NO: 1, amino acids 20-144
:::::::::::::::::::::::::::::::.::::::::::::::::::. ::: .: .
QVQLVESGGGVVQPGRSLRLSCAASGFTFSSYGMHWVRQAPGKGLEWVAVILYDGSNKYH    SEQ ID NO: 15
        10        20        30        40        50        60
```

TABLE 3-continued

Comparison of Heavy Chain Variable Regions

```
         70        80        90       100       110       120
ADSVKGRFTISRDNSKNTLYLQMNSLRTEDTAVYFCARERFSGAYFDYWGQGTLVTVSSA
::::::::::::::::::::::::::::.:::::::::.::.  :::::::::::::::
ADSVKGRFTISRDNSKNTLYLQMNSLRAEDTAVYYCARIAPAGSAFDYWGQGTLVTVSSA
         70        80        90       100       110       120

STKGP
:::::
STKGP
```

TABLE 4

Comparison of Light Chain Variable Regions

```
Comparison of:
17c7L                               -107 aa
6G11L                               -106 aa
using matrix file: BLOSUM50, gap penalties: -14/-4
71.7% identity in 106 aa overlap; score:    527

10        20        30        40        50        60
IVLTQSPATLSLSPGERATLSCRASQSVSSYLAWYQQKPGQAPRLLIYDASNRATGIPAR    SEQ ID NO: 2, amino acids 22-127
: :::::::.:: : :..::..:::  :::::..:  :::::: :.:.::::::  .::.:
IQLTQSPSSLSASVGDRVTITCRASQGISSVLAWYQQKSGKAPKFLIYDASSLESGVPSR   SEQ ID NO: 16, amino acids 2-105
        10        20        30        40        50        60

70        80        90       100
FSGSGSGTDFTLTISSLEPEDFAVYSCQQRNNWPPTFGGGTKVEIK
:::::::::::::::::::.::::::.:::  :..:::: :::.:::
FSGSGSGTDFTLTISSLQPEDFATYYCQQFNSYPPTFGQGTKLEIK
```

Exemplary CDRs derivative or consensus sequences are presented below.

TABLE 5

Heavy Chain CDR Derivatives

| CDR | Formula | Modifications |
|---|---|---|
| CDR1 | GFTFSX1YX2MH<br>SEQ ID NO: 29 | X can be any amino acid<br>or X1 = T/S; X2 = A/G |
| CDR2 | VAVX1X2YDGX3X4KX5X6AD<br>SVKG<br>SEQ ID NO: 30 | X can be any amino acid<br>or X1 = V/I; X2 = S/L;<br>X3 = R/S; X4 = I/N;<br>X5 = D/Y; X6 = Y/H |
| CDR3 | ARX1X2X3GX4X5FDY<br>SEQ ID NO: 31 | X can be any amino acid<br>or X1 = E/I; X2 = R/A;<br>X3 = F/P; X4 = A/S;<br>X5 = Y/S |

TABLE 6

Light Chain CDRs Derivatives

| CDR | Formula | Modifications |
|---|---|---|
| CDR1 | RASQX1X2SSX3L<br>SEQ ID NO: 32 | X can be any amino acid<br>or X1 = S/G; X2 = V/I;<br>X3 = Y/V |
| CDR2 | DASX1X2X3X4<br>SEQ ID NO: 33 | X can be any amino acid<br>or X1 = N/S1; X2 = R/L;<br>X3 = A/E; X4 = T/S |
| CDR3 | CQQX1NX2X3P<br>SEQ ID NO: 34 | X can be any amino acid<br>or X1 = R/F; X2 = N/S;<br>X3 = W/Y |

It is also understood that one more of the CDRs disclosed herein (including CDR derivative or consensus sequences) can be used for identifying naturally occurring CDRs that are suitable for binding to a rabies virus epitope. The CDRs can also be combined or cross-cloned between variable regions, for example, light chain CDRs can be introduced into heavy chain variable regions and heavy chain CDRs can be introduced into light chain variable regions and screened to insure that specific binding is retained.

Human anti-rabies virus antibodies can include variable regions that are the product of, or derived from, specific human immunoglobulin genes. For example, the antibodies can include a variable heavy chain region that is the product of, or derived from, a human VH 3-30-3 or VH3-33 gene (see, e.g., Acc. No.: AJ555951, GI No.: 29836865; Acc. No.: AJ556080, GI No.: 29837087; Acc. No.: AJ556038, GI No.: 29837012, and other human VH3-33 rearranged gene segments provided in GenBank®). The antibodies can also, or alternatively, include a light chain variable region that is the product of, or derived from a human Vκ L6, Vκ L11, Vκ L13, Vκ L15, or Vκ L19. gene (see, e.g., GenBank® Acc. No.: AJ556049, GI No.: 29837033 for a partial sequence of a rearranged human Vκ L19 gene segment). As known in the art, and described in this section, above, variable immunoglobulin regions of recombined antibodies are derived by a process of recombination in vivo in which variability is introduced to genomic segments encoding the regions. Accordingly, variable regions derived from a human VH or VL gene can include nucleotides that are different that those in the gene found in non-lymphoid tissues. These nucleotide differences are typically concentrated in the CDRs.

Moreover, the above antibodies exhibit binding activity to a rabies virus and, in particular, to one or more rabies G glycoprotein epitopes. Such antibodies further exhibit rabies virus neutralization activity and in vivo protective efficacy against rabies sequelae as further described below and in the examples.

2. Production and Modification of Antibodies

Many different forms of anti-rabies virus antibodies can be useful in the inhibition of rabies virus-mediated disease. The antibodies can be of the various isotypes, including: IgG (e.g., IgG1, IgG2, IgG3, IgG4), IgM, IgA1, IgA2, IgD, or IgE. Preferably, the antibody is an IgG isotype, e.g., IgG1. The antibody molecules can be full-length (e.g., an IgG1, IgG2, IgG3, or IgG4 antibody) or can include only an antigen-binding fragment (e.g., a Fab, $F(ab')_2$, Fv or a single chain Fv fragment). These include monoclonal antibodies (e.g., human monoclonal antibodies), recombinant antibodies, chimeric antibodies, and humanized antibodies, as well as antigen-binding portions of the foregoing.

Anti-rabies virus antibodies or portions thereof useful in the present invention can also be recombinant antibodies produced by host cells transformed with DNA encoding immunoglobulin light and heavy chains of a desired antibody. Recombinant antibodies may be produced by known genetic engineering techniques. For example, recombinant antibodies can be produced by cloning a nucleotide sequence, e.g., a cDNA or genomic DNA, encoding the immunoglobulin light and heavy chains of the desired antibody. The nucleotide sequence encoding those polypeptides is then inserted into an expression vector so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is preferred because such cells are more likely than prokaryotic cells to assemble and secrete a properly folded and immunologically active antibody. However, any antibody produced that is inactive due to improper folding can be renatured according to well known methods (Kim and Baldwin, *Ann. Rev. Biochem.*, 51:459-89, 1982). It is possible that the host cells will produce portions of intact antibodies, such as light chain dimers or heavy chain dimers, which also are antibody homologs according to the present invention.

The antibodies described herein also can be produced in a host cell transfectoma using, for example, a combination of recombinant DNA techniques and gene transfection methods as is well known in the art (Morrison, S., *Science,* 229:1202, 1985). For example, in one embodiment, the gene(s) of interest, e.g., human antibody genes, can be ligated into an expression vector such as a eukaryotic expression plasmid such as used in a GS gene expression system disclosed in WO 87/04462, WO 89/01036 and EP 338 841, or in other expression systems well known in the art. The purified plasmid with the cloned antibody genes can be introduced in eukaryotic host cells such as CHO-cells or NS0-cells or alternatively other eukaryotic cells like a plant derived cells, fungi, or yeast cells. The method used to introduce these genes can be any method described in the art, such as electroporation, lipofectine, Lipofectamine, transfection (e.g., calcium chloride-mediated), or ballistic transfection, in which cells are bombarded with microparticles carrying the DNA of interest (Rodin, et al. *Immunol. Lett.,* 74(3):197-200, 2000). After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells using standard techniques.

It will be understood that variations on the above procedures are useful in the present invention. For example, it may be desired to transform a host cell with DNA encoding either the light chain or the heavy chain (but not both) of an antibody. Recombinant DNA technology may also be used to remove some or all of the DNA encoding either or both of the light and heavy chains that is not necessary for binding, e.g., the constant region may be modified by, for example, deleting specific amino acids. The molecules expressed from such truncated DNA molecules are useful in the methods described herein. In addition, bifunctional antibodies can be produced in which one heavy and one light chain bind to a rabies virus, and the other heavy and light chain are specific for an antigen other than the rabies virus, or another epitope of the rabies virus.

Also within the scope of the invention are antibodies in which specific amino acids have been substituted, deleted, or added. In particular, preferred antibodies have amino acid substitutions in the framework region, such as to improve binding to the antigen. For example, a selected, small number of acceptor framework residues of the immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089 (e.g., columns 12-16), the contents of which are hereby incorporated by reference. The acceptor framework can be a mature human antibody framework sequence or a consensus sequence. As desired, the Fc region of antibodies of the invention can be altered to modulate effector function(s) such as, for example, complement binding and/or Fc receptor binding. Criteria and subsets of framework alterations and/or constant regions suitable for alteration (by, e.g., substitution, deletion, or insertion) are described in U.S. Pat. Nos. 6,548,640; 5,859,205; 6,632,927; 6,407,213; 6,054,297; 6,639,055; 6,737,056; and 6,673,580.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

An anti-rabies virus antibody, or antigen-binding portion thereof, can be derivatized or linked to another functional molecule (e.g., another peptide or protein). For example, an antibody can be functionally linked (by chemical coupling, genetic fusion, noncovalent association or otherwise) to one or more other molecular entities, such as another antibody, a detectable agent, a cytotoxic agent, a pharmaceutical agent, and/or a protein or peptide that can mediate association with another molecule (such as a streptavidin core region or a polyhistidine tag).

One type of derivatized antibody (or fragment thereof) is produced by crosslinking two or more of such proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which a antibody (or fragment thereof) can be derivatized (or labeled) include fluorescent compounds, various enzymes, prosthetic groups, luminescent materials, bioluminescent materials, and radioactive materials. Exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, β-galactosidase, acetylcholinesterase, glucose oxidase and the like. When a protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A protein can also be derivatized with a prosthetic group (e.g., streptavidin/biotin and avidin/biotin). For example, an antibody can be derivatized with biotin, and detected through indirect measurement of avidin or streptavidin binding.

Labeled proteins and antibodies can be used, for example, diagnostically and/or experimentally in a number of contexts, including (i) to isolate a predetermined antigen by standard techniques, such as affinity chromatography or immunoprecipitation; and (ii) to detect a predetermined antigen (e.g., a rabies virus, or rabies virus protein, carbohydrate, or lipid, or combination thereof, e.g., in a cellular lysate or a patient sample) in order to monitor virus and/or protein levels in tissue as part of a clinical testing procedure, e.g., to determine the efficacy of a given treatment regimen.

Any of the above protein derivatizing/labeling techniques can also be employed on a viral target, for example, a rabies protein, such as a G glycoprotein or fragment(s) thereof.

3. Screening Methods

Anti-rabies virus antibodies can be characterized for binding to the rabies virus by a variety of known techniques. Antibodies are typically characterized by ELISA first. Briefly, microtiter plates can be coated with the target antigen in PBS, for example, the rabies virus or G glycoprotein or portion thereof, and then blocked with irrelevant proteins such as bovine serum albumin (BSA) diluted in PBS. Dilutions of plasma from mice immunized with the target antigen, for example, a rabies vaccine, are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with rabies virus. Hybridomas that produce antibodies that bind, preferably with high affinity, to rabies virus can than be subcloned and further characterized. One clone from each hybridoma, which retains the reactivity of the parent cells (by ELISA), can then be chosen for making a cell bank, and for antibody purification.

To purify the anti-rabies virus antibodies, selected hybridomas can be grown in roller bottles, two-liter spinner-flasks or other culture systems. Supernatants can be filtered and concentrated before affinity chromatography with protein A-Sepharose (Pharmacia, Piscataway, N.J.) to purify the protein. After buffer exchange to PBS, the concentration can be determined by spectrophotometric methods.

To determine if the selected monoclonal antibodies bind to unique epitopes, each antibody can be biotinylated using commercially available reagents (Pierce, Rockford, Ill.). Biotinylated MAb binding can be detected with a streptavidin labeled probe. Anti-rabies virus antibodies can be further tested for reactivity with the rabies virus or rabies virus protein by immunoprecipitation or immunoblot.

Particular antibodies of the invention are characterized as binding to one or more epitope of a rabies G glycoprotein. For example, the rabies G glycoprotein epitope can be a linear epitope, conformational epitope, discontinuous epitope, or combinations of such epitopes.

In one embodiment, the rabies G glycoprotein epitope consists of antigenic site I, antigenic site II, antigenic site III, antigenic site minor A, or combinations of such antigenic sites, for example, antigenic site III and minor site A.

In another embodiment, the epitope of the rabies G glycoprotein comprises amino acid residues 336-442. In a particular embodiment, the rabies G glycoprotein comprises amino acid residue 336 and, optionally, alterations thereof such as substitutions or deletions (e.g., see Table 9).

Other assays to measure activity of the anti-rabies virus antibodies include neutralization assays. In vitro neutralization assays can measure the ability of an antibody to inhibit a cytopathic effect, infectivity, or presence of a virus on or in cells in culture (see Example 3, below). In vivo neutralization or survival assays can be used to measure rabies virus neutralization as a function of reduced morbidity and/or mortality in an appropriate animal model (see Examples 5, below).

4. Pharmaceutical Compositions and Kits

In another aspect, the present invention provides compositions, e.g., pharmaceutically acceptable compositions, which include an antibody molecule described herein or antigen binding portion thereof, formulated together with a pharmaceutically acceptable carrier.

"Pharmaceutically acceptable carriers" include any and all solvents, dispersion media, isotonic and absorption delaying agents, and the like that are physiologically compatible. The carriers can be suitable for intravenous, intramuscular, subcutaneous, parenteral, rectal, spinal, or epidermal administration (e.g., by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Useful compositions are in the form of injectable or infusible solutions. A useful mode of administration is parenteral (e.g., intravenous, subcutaneous, intraperitoneal, intramuscular). For example, the antibody or antigen binding portion thereof can be administered by intravenous infusion or injection. In another embodiment, the antibody or antigen binding portion thereof is administered by intramuscular or subcutaneous injection.

The composition of the invention may be co-administered with a) one or more other antibodies, e.g., anti-rabies antibodies, b) rabies protein, e.g., a rabies vaccine, c) toxin(s) d) other therapeutic agent(s) (e.g., antivirals), and/or e) label(s).

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intracranial, intraperitoneal, transtracheal, subcutaneous, subcuticular, intraarticular, subcapsular, subarachnoid, intraspinal, epidural, and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the useful methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody portions described herein can be administered by a variety of methods known in the art, and for many therapeutic applications. As will be appreciated by the skilled artisan, the route and/or mode of administration will vary depending upon the desired results.

In certain embodiments, an antibody, or antibody portion thereof may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can be administered with medical devices known in the art.

Dosage regimens are adjusted to provide the optimum desired response (e.g., a therapeutic response). For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or antigen binding portion of the invention is 0.1-60 mg/kg, e.g., 0.5-25 mg/kg, 1-2 mg/kg, or 0.75-10 mg/kg. In one embodiment, the amount of anti-rabies virus antibody (or antigen binding portion thereof) administered, is at or about 0.125 mg/kg, 0.25 mg/kg, 0.5 mg/kg, or at an interval or range thereof. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Also within the scope of the invention are kits including an anti-rabies virus antibody or antigen binding portion thereof. The kits can include one or more other elements including: instructions for use; other reagents, e.g., a label, a therapeutic agent, or an agent useful for chelating, or otherwise coupling, an antibody to a label or therapeutic agent, or other materials for preparing the antibody for administration; pharmaceutically acceptable carriers; and devices or other materials for administration to a subject.

Various combinations of antibodies can be packaged together. For example, a kit can include antibodies that bind to rabies virus (e.g., antibodies that include the variable heavy and/or light chain regions of 17C7, 6G11, 5G5, 2B10, E5, or a combination thereof. The antibodies can be mixed together, or packaged separately within the kit.

Instructions for use can include instructions for therapeutic application including suggested dosages and/or modes of administration, e.g., in a patient with a symptom or indication of rabies virus exposure or suspected of rabies virus exposure. Other instructions can include instructions on coupling of the antibody to a chelator, a label or a therapeutic agent, or for purification of a conjugated antibody, e.g., from unreacted conjugation components.

The kit can include a detectable label, a therapeutic agent, and/or a reagent useful for chelating or otherwise coupling a label or therapeutic agent to the antibody. Coupling agents include agents such as N-hydroxysuccinimide (NHS). In such cases the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional anti-rabies virus antibodies (or portions thereof), formulated as appropriate, in one or more separate pharmaceutical preparations.

Other kits can include optimized nucleic acids encoding anti-rabies virus antibodies, for use as passive immunotherapy, and/or rabies virus protein(s), or fragments thereof, for use as, e.g., vaccines (active immunotherapy), and instructions for expression of the nucleic acids.

5. Therapeutic Methods and Compositions

Antibodies and antibody binding fragments of the present invention have in vitro and in vivo therapeutic, prophylactic, and diagnostic utilities. For example, these antibodies can be administered to cells in culture, e.g., in vitro or ex vivo, or in vivo, to an animal, preferably a human subject, to treat, inhibit, prevent relapse, and/or diagnose rabies virus and disease associated with rabies.

As used herein, the term "subject" is intended to include human and non-human animals. The term "non-human animals" includes all vertebrates, e.g., mammals and non-mammals, such as non-human primates, mice, dogs, cats, pigs, cows, and horses.

The proteins and antibodies can be used on cells in culture, e.g., in vitro or ex vivo. For example, cells can be cultured in vitro in culture medium and the contacting step can be effected by adding the anti-rabies virus antibody or fragment thereof, to the culture medium. The methods can be performed on virions or cells present in a subject, as part of an in vivo (e.g., therapeutic or prophylactic) protocol. For in vivo embodiments, the contacting step is effected in a subject and includes administering an anti-rabies virus antibody or portion thereof to the subject under conditions effective to permit binding of the antibody, or portion, to a rabies virus or any portion thereof present in the subject, e.g., in or around a wound or on or near cells of neuronal origin.

Methods of administering antibody molecules are described herein. Suitable dosages of the molecules used will depend on the age and weight of the subject and the particular drug used. The antibody molecules can be used as competitive agents for ligand binding to inhibit or reduce an undesirable interaction, e.g., to inhibit binding and/or infection of rabies virus of cells, e.g., neuronal cells.

The anti-rabies virus antibodies (or antigen binding portions thereof) can be administered in combination with other anti-rabies virus antibodies (e.g., other monoclonal antibodies, polyclonal gamma-globulin, e.g., human serum comprising anti-rabies immunoglobulins). Combinations of antibodies that can be used include an anti-rabies virus antibody or antigen binding portion thereof and/or an anti-rabies virus G protein antibody or antigen binding portion thereof. The anti-rabies virus or G protein antibody can be antibody clone 17C7, 6G11, 5G5, 2B10, and/or E5 that includes the variable regions of such an antibody or antibodies, or an antibody with variable regions at least 90% identical to the variable regions of such an antibody or antibodies. In one embodiment, the anti-rabies virus antibody can be 17C7 or portion thereof or an antibody with variable regions at least 90% identical to the variable regions of the foregoing, e.g., 17C7, 6G11, 5G5, 2B10, and/or E5. Combinations of anti-rabies virus antibodies (e.g., 17C7, 6G11, 5G5, 2B10, and/or E5) can provide potent inhibition of rabies, especially, e.g., particular rabies isolates (see Tables 11-13). Characteristic rabies virus isolates for which the antibodies of the invention are suitable for treating, detecting, diagnosing and the like include, for example, CVS-11 isolate, ERA isolate, Pasteur virus isolate, gray fox (Texas) isolate, gray fox (Arizona) isolate, arctic fox (Arkansas) isolate, skunk (North Central) isolate, skunk (South Central) isolate, raccoon isolate, coyote (Texas) isolate, dog (Texas) isolate, bat (*Lasiurus borealis*; Tennessee) isolate, bat (*Eptesicus fuscus-Myotis* spp.; Colorado) isolate, bat (*Myotis* spp.; Washington) isolate, bat (*Lasiurus cinereus*; Arizona) isolate, bat (*Pipistrellus subflavus*; Alabama) isolate, bat (*Tadarida brasiliensis*; Alabama) isolate, bat (*Lasionycetris noctivagans*; Washington) isolate, bat (*Eptesicus fuscus*; Pennsylvania) isolate, mongoose (New York/Puerto Rico) isolate, dog (Argentina) isolate, dog (Sonora) isolate, dog (Gabon) isolate, dog (Thai) isolate, and combinations thereof.

It is understood that any of the agents of the invention, for example, anti-rabies virus antibodies, or fragments thereof, can be combined, for example in different ratios or amounts, for improved therapeutic effect. Indeed, the agents of the invention can be formulated as a mixture, or chemically or genetically linked using art recognized techniques thereby resulting in covalently linked antibodies (or covalently linked antibody fragments), having anti-rabies binding properties, for example, multi-epitope binding properties to, for example, rabies virus G glycoprotein. The combined formulation may be guided by a determination of one or more parameters such as the affinity, avidity, or biological efficacy of the agent alone or in combination with another agent. The agents of the invention can also be administered in combination with other agents that enhance access, half-life, or stability of the therapeutic agent in targeting, clearing, and/or sequestering rabies virus or an antigen thereof.

Such combination therapies are preferably additive and even synergistic in their therapeutic activity, e.g., in the inhibition, prevention, infection, and/or treatment of rabies virus-related disease or disorders. Administering such combination therapies can decrease the dosage of the therapeutic agent (e.g., antibody or antibody fragment mixture, or cross-linked or genetically fused bispecific antibody or antibody fragment) needed to achieve the desired effect.

Immunogenic compositions that contain an immunogenically effective amount of a rabies virus component, for example, rabies virus G glycoprotein, or fragments thereof, also provided by the present invention, and can be used in generating anti-rabies virus antibodies. Immunogenic epitopes in a rabies virus protein sequence can be identified as described herein (see e.g. Example 4) or according to methods known in the art, and proteins, or fragments containing those epitopes can be delivered by various means, in a vaccine composition. Suitable compositions can include, for example, lipopeptides (e.g., Vitiello et al., *J. Clin. Invest.* 95:341 (1995)), peptide compositions encapsulated in poly (DL-lactide-co-glycolide) ("PLG") microspheres (see, e.g., Eldridge et al., *Molec. Immunol.* 28:287-94 (1991); Alonso et al., *Vaccine* 12:299-306 (1994); Jones et al., *Vaccine* 13:675-81 (1995)), peptide compositions contained in immune stimulating complexes (ISCOMS) (see, e.g., Takahashi et al., *Nature* 344:873-75 (1990); Hu et al., *Clin. Exp. Immunol.* 113:235-43 (1998)), and multiple antigen peptide systems (MAPs) (see, e.g., Tam, *Proc. Natl. Acad. Sci. U.S.A.* 85:5409-13 (1988); Tam, *J. Immunol. Methods* 196:17-32 (1996)).

Useful carriers that can be used with immunogenic compositions of the invention are well known, and include, for example, thyroglobulin, albumins such as human serum albumin, tetanus toxoid, polyamino acids such as poly L-lysine, poly L-glutamic acid, influenza, hepatitis B virus core protein, and the like. The compositions can contain a physiologically tolerable (i.e., acceptable) diluent such as water, or saline, typically phosphate buffered saline. The compositions and vaccines also typically include an adjuvant. Adjuvants such as incomplete Freund's adjuvant, aluminum phosphate, aluminum hydroxide, or alum are examples of materials well known in the art. Additionally, CTL responses can be primed by conjugating target antigens, for example a rabies virus protein(s) (or fragments, inactive derivatives or analogs thereof) to lipids, such as tripalmitoyl-S-glycerylcysteinyl-seryl-serine ($P_3CSS$).

The anti-rabies antibodies can be administered in combination with other agents, such as compositions to treat rabies virus-mediated disease. For example, therapeutics that can be administered in combination with anti-rabies antibodies include antiviral agents, serum immunoglobulin, and/or vaccines for treating, preventing, or inhibiting rabies (for example, vaccines such as RabAvert™ (Chiron), Rabies vaccine adsorbed (Bioport), and Imovax™ Rabies (Aventis) and/or immunoglobulins, such as BayRab™ (Bayer) and Imogam™ Rabies-HT (Aventis). The antibody can be administered before, after, or contemporaneously with a rabies virus vaccine.

6. Other Methods

An anti-rabies antibody (e.g., monoclonal antibody) can be used to isolate rabies virus by standard techniques, such as affinity chromatography or immunoprecipitation. Moreover, an anti-rabies antibody can be used to detect the virus (e.g., in a serum sample), e.g., to screen samples for the presence/exposure of rabies virus. Anti-rabies antibodies can be used diagnostically to monitor levels of the virus in tissue as part of a clinical testing procedure, e.g., to, for example, determine the efficacy of a given treatment regimen. In addition, rabies virus epitopes, for example, G glycoprotein epitopes (linear, conformational, or combinations thereof) can be used as immunogens or as targets to identify neutralizing anti-rabies binding molecules, including, for example, human serum, polyclonal antibodies, monoclonal antibodies, or fragments thereof.

Exemplification

Throughout the examples, the following materials and methods were used unless otherwise stated.

Materials and Methods

In general, the practice of the present invention employs, unless otherwise indicated, conventional techniques of chemistry, molecular biology, recombinant DNA technology, immunology (especially, e.g., antibody technology), and standard techniques in polypeptide preparation. See, e.g., Sambrook, Fritsch and Maniatis, *Molecular Cloning: Cold Spring Harbor Laboratory Press* (1989); *Antibody Engineering Protocols* (*Methods in Molecular Biology*), 510, Paul, S., Humana Pr (1996); *Antibody Engineering: A Practical Approach* (Practical Approach Series, 169), McCafferty, Ed., Irl Pr (1996); *Antibodies: A Laboratory Manual*, Harlow et al., C.S.H.L. Press, Pub. (1999); and *Current Protocols in Molecular Biology*, eds. Ausubel et al., John Wiley & Sons (1992). See also, e.g., Smith et al., *A rapid fluorescent focus inhibition test (RFFIT) for determining rabies virus-neutralizing antibody*, pages 181-189 and Chapter 15 in *Laboratory Techniques in Rabies*, 4th ed., edited by Meslin et al., Geneva: World Health Organization (1996)).

Mouse Immunization and Isolation of Hybridomas

HuMab mice (Medarex) are transgenic mice containing human immunoglobulin genes and inactivated mouse heavy chain genes and kappa light chain genes. HuMab mice were typically injected with a~1/10 of a human dose of a commercially available rabies vaccine using complete Freund's adjuvant in the first week, and RIBI adjuvant in subsequent weeks for a total of 6-8 weeks. A rabies envelope glycoprotein ELISA was used to measure serum responses and animals were sacrificed when serum responses were considered maximal. Hybridomas were generated by fusion of splenocytes and partner cells (P3X63Ag8.653 mouse myeloma cells) and resultant supernatants were screened for reactivity in a rabies glycoprotein ELISA. Positive antibodies were purified from hybridoma cultures by protein A Sepharose chromatography (Amersham).

RFFIT

The RFFIT assay was performed as described in the art. The rabies virus strains, street virus isolates, and mouse neuroblastoma cells (MNA) used were all from the Center from Disease Control and Prevention, Atlanta, USA.

Cells and Cell Culture

HEK-293T/17 cells, obtained from the ATCC, were grown in Dulbecco's modified Eagle's medium (DMEM) supplemented with 10% fetal bovine serum and 100 IU of penicillin-streptomycin (complete medium) at 37° C. with 5% $CO_2$. Cells were harvested in phosphate buffered saline (PBS) containing 5 mM EDTA.

Cloning of Rabies Glycoproteins

The amino acid sequence of the rabies G protein (ERA strain, Genbank: AF406693) was used to design a codon-optimized version of the rabies glycoprotein gene spanning the full length glycoprotein from amino acid 1-524. The synthetic gene was cloned into pcDNA3.1Myc/His (Invitrogen) in frame with the c-Myc and 6-histidine (His) tags. These immunotags enabled easy purification and detection. Truncated versions of the tagged glycoprotein-encoding genes were constructed which contained the entire ectodomain (20-439 a.a.). Truncations were made by PCR amplification of the desired fragments from the full length glycoprotein clones followed by restriction digestion and ligation into pcDNA3.1Myc/His (Invitrogen) and verified by DNA sequence analysis.

For the isolation of native genes encoding various strains of rabies G glycoproteins, MNA cells were infected with the CVS-11, Skunk-CA, *Lasirius borealis, Lasirius cinereus*, and ERA rabies viruses (Center for Disease Control and Prevention, USA). RNA was extracted from infected cells or from virions using Trizol reagent. RTPCR was performed in 2 steps. First, cDNA was synthesized using the Ambion Retroscript Kit, and the rabies glycoprotein-encoding genes were then amplified using Turbo Pfu (Stratagene) and rabies virus specific primers. The rabies glycoprotein encoding genes were cloned into the mammalian expression vector pCDNA3.1MycHis (Invitrogen) at the HindIII/Xba I sites in frame with the c-Myc and His epitope tags. Recombinant genes encoding rabies glycoprotein mutated at residues classified as antigenic site I, II, III and minor site a were synthesized using site-directed mutagenesis. Overlapping primers containing the desired point mutations were used to amplify full length mutant glycoprotein genes and the pcDNA3.1Myc/His vector from the previously cloned codon-optimized ERA glycoprotein. The PCR amplified DNA was digested with DpnI to remove the wild type non-amplified starting template, transformed into bacteria, and screened for the intended mutation by sequencing. The full coding sequence of each mutant was confirmed, and the resulting constructs were cloned into pcDNA3.1Myc/His expression vectors.

Recombinant Glycoprotein Expression

All constructs were transfected into HEK-293T/17 cells using Lipofectamine 2000 (Invitrogen) as described by the manufacturer. Cells were grown to 85% confluence in 150 mm tissue culture dishes in 15 ml of DMEM-10% fetal calf serum (FCS). Amounts of 30 ug of DNA mixed with 75 ul of Lipofectamine were added to the cells, and plates were incubated overnight at 37° C. Media was removed and stored at 24, 48 and 72 hours post-transfection for secreted soluble proteins or discarded for membrane bound proteins.

Recombinant Protein Purification, Immunoprecipitation and Western Blot

Rabies glycoproteins ERA20-439 and CVS-1120-439, both containing Myc and His epitope tags, were purified from cell culture supernatant by incubation with nickel-nitrilotriacetic acid (Ni-NTA) beads (Invitrogen), followed by column filtration and protein elution using 250 mM imidazole. For immunoprecipitation of full-length membrane bound glycoproteins, transfected cells were detached from the plate with PBS/5 mM EDTA and solubilized in PBS, 1% CHAPS, 1× complete proteinase inhibitor. Cellular lysates were cleared by centrifugation and incubated with either HuMab 17C7, or a control non-rabies HuMab, and Protein A Sepharose. Immunoprecipitated proteins were resolved by SDS-PAGE for subsequent analysis.

For immunoblot analysis, proteins were boiled in 2× Laemmli sample buffer (+/−BME) for 5 minutes and resolved using 10 or 12% Novex gels (Invitrogen). Gels were transferred to Immobilon P (Millipore) as described by the manufacturer, and immunoblot analysis was performed. Proteins were detected using the mouse anti-Myc antibody 9E10 (0.2 ug/ml) (BD Pharmingen), or HuMab 17C7 (2 ug/ml) followed by horseradish peroxidase-conjugated anti-mouse or anti-human IgG (1:5000 Jackson Immuoresearch). Membranes were incubated with enhanced chemiluminescence reagent (Amersham) for 1 minute and exposed to X-Omat-AR film for various periods of time.

Cell Surface Staining

Cells transfected with constructs encoding full-length rabies G protein were harvested 48 hours post-transfection and incubated with varying concentration of HuMabs. Binding of the HuMabs was detected by phycoerythrin labeled anti-human IgG (Jackson) and flow cytometry was performed using FACScan with CellQuest software (Becton Dickinson).

ELISAs

A capture ELISA was performed on all hybridomas to identify those making human IgG. ELISA plates were coated with 3 μg/ml of goat anti-human kappa light chain antibodies (Southern Biotech). Plates were washed with wash buffer (PBS, 0.05% Tween), blocked with blocking buffer (PBS, 1% BSA, 0.05% Tween), washed, and then samples were added to plate (diluted 1:2-1:400 in blocking buffer). Binding was detected with goat anti-human IgG-AP secondary antibody (Jackson ImmunoResearch), and the plates were washed and developed with p-Nitrophenyl phosphate disodium salt at 1 mg/ml in 1M diethanolamine for 20 minutes. The plates were read at 405 nm.

A capture glycoprotein ELISA was used to test the interaction of HuMab 17C7 with CVS-1120-439 and codon optimized ERA20-439. Plates were coated with 7.5 ug/ml of mouse anti-c-Myc antibody 9E10 (BD Pharmingen) or chicken anti-c-Myc antibody (Molecular Probes). Plates were incubated with purified glycoproteins or detergent solubilized cell lysates, and then incubated with primary antibodies (HuMab 17C7 and mouse anti-rabies glycoprotein R0012 (US Biological)) at 5 ug/ml. Binding was detected with alkaline phosphatase conjugated goat anti-human secondary (Jackson ImmunoResearch), and then developed as described above.

Production of HuMab 17C7 Resistant Viruses

Mouse neuroblastoma cells were plated at $1.5 \times 10^5$ cells/ml well on Day 1. On Day 2 $1 \times 10^1$ to $10^8$ FFU/ml of CVS-11 rabies virus was incubated with IU/ml of HuMab 17C7 (133 ug/ml) at 37° C. for 1 hour. The virus/antibody mix was added to the cells and incubated for 3-12 hours at 37° C. The virus/antibody mix was removed from the cells and cells were washed once with media, followed by addition of fresh media containing IU/ml of HuMab 17C7 for an additional 60 hours. On Day 5 the media, containing potential HuMab 17C7 resistant virus, was removed from the slides, labeled and stored at 4° C. Slides were then stained for presence of rabies infected cells by incubation with 1:40 dilution of Centicor FITC anti-Rabies IgG (Fujirebio Diagnostics) for 30 minutes at 36° C./0.5% CO2. The slides were then washed and examined under a fluorescent microscope (FITC filter) at 200× magnification. Virus taken from wells containing 1-5 fluorescent foci were amplified on MNA cells for 3 days in the presence of HuMab 17C7. The amplified virus was tested for the ability to infect MNA cells equivalently in the presence and absence of HuMab 17C7. 6-well plates of MNA cells were infected with the HuMab 17C7 resistant virus. RNA was extracted from virus-infected cells, reverse transcribed, and the glycoprotein-encoding sequence was PCR amplified with CVS-11 glycoprotein-specific primers. The mutations in glycoprotein-encoding genes were analyzed by sequencing the entire coding sequence.

Rabies Pseudovirus

A replication defective Env-, Vpr-HIV backbone containing the firefly luciferase gene inserted into the nef gene, pNL4-3.Luc.R-E-, was co-transfected with rabies glycoprotein encoding plasmids into 293T cells. The pNL4-3.Luc.R-E-reagent was obtained through the NIH AIDS Research and Reference Reagent Program, Division of AIDS, NIAID, and NIH. Pseudoviral particles were harvested 48-72 hours post-transfection, concentrated 30-fold using a centricon concentrator (Millipore) and frozen at −80° C. The luciferase counts per second of the pseudovirus preparations were determined by serial dilution of the virus followed by infection and detection (see below). For the neutralization assays approximately 50,000 counts per second of pseudovirus were incubated with and without antibody for 1 hour at room temperature. The antibody/virus mix was then applied to HOS cells (ATCC #CRL-1543), in the presence of 2 ug/ml of polybrene and spinoculated for 2 hours at 800 G and 4° C., followed by incubation at 37° C./5% CO2. Luciferase activity was then assayed 72 hours post-infection using the Bright-Glo reagent (Promega), according to the manufacturer's protocol.

EXAMPLES

The invention is further described in the following examples, which do not limit the scope of the invention described in the claims.

Example 1

Generation of Anti-Rabies Virus Monoclonal Antibodies

Transgenic mice comprising human immunoglobulin genes generated as described above in the section entitled "Generation of Human Monoclonal Antibodies in HuMAb Mice" and supplied by Medarex, Milpitas, Calif., were immunized with 6 doses of a commercial rabies vaccine. The vaccine was administered in combination with Fruend's complete adjuvant and then boosted with additional rabies vaccine and incomplete Fruend's adjuvant. The rabies vaccine consists of whole rabies virus that has been inactivated and lyophilized. Spleenic B cells were isolated from the immunized animal and fused to mouse myeloma (P3X) cells. Clonal hybridomas were generated and screened by ELISA. Resultant hybridomas were cultured and enzyme linked immunosorbent assay (ELISA) for detection of human kappa/gamma antibody chains was used to detect candidate human IgG antibodies for further analysis. Clones designated 54.17C7; 108.6G11; 35.5G5.1E12.149; 35.2B10.1G11.3FG; and 35.1E51G1.4CB referred to herein as, respectively, clones 17C7, 6G11, 5G5, 2B10, and 1E5 were further determined to specifically bind rabies virus G glycoprotein by an antigen specific ELISA assay. In addition, these five hybridoma clones were selected and determined to neutralize rabies infection of mouse neuronal cells in a RFFIT assay against a number of different rabies isolates (see Example 3).

Accordingly, cDNAs from exemplary clones were amplified by RT-PCR from mRNA, cloned, and sequenced. One heavy chain V region consensus sequence was found for each clone (Table 7). All five clones utilized a VH region derived from one of two germline V region genes, but utilized different J sequences. The amino acid sequences of the VH and VL regions from exemplary clones 17C7 and 6G11 are shown in FIGS. 1-2 (SEQ ID NOs: 1, 2, 15, and 16). The complementarity determining regions (i.e., CDR1, CDR2, and CDR3) are indicated for the antibody heavy and light chain variable regions (SEQ ID NOs: 3-8; 17-22). DNA encoding the antigen binding portion of each clone was cloned into a vector to be expressed as a human antibody for administration to humans. The nucleic acid and amino acid sequences for the light and heavy chains of antibody clones 17C7 and 6G11 are provided in the sequence listing (respectively, SEQ ID NOs: 9-12 and SEQ ID NOs: 23-26).

TABLE 7

Antibody Clones and Gene Composition

| HuMab | Clone Designation | HuMab mouse genotype |
|---|---|---|
| 54.17C7 | 17C7 | Female Hco12 |
| 108.6G11 | 6G11 | Male Hco7 |
| 35.5G5 | 5G5 | Male Hco7 |
| 35.1E5 | 1E5 | Male Hco7 |
| 35.2B10 | 2B10 | Male Hco7 |

| HuMab | Variable region light chain | | Variable region heavy chain | | |
|---|---|---|---|---|---|
| 54.17C7 | VK: IGKV3-11*01 | JK: IGKJ4*01 | VH: IGHV3-30-3*01 | D: IGHD3-3*01 | JH: IGHJ4*02 |
| 108.6G11 | VK: IGKV1-13*02 | JK: IGKJ2*02 | VH: IGHV3-33*05 | D: IGHD6-13*01 | JH: IGHJ4*02 |

(*IMGT nomenclature used for above table)

Example 2

Binding Activity of Anti-Rabies Virus Antibodies

Binding of each antibody to rabies virus, in particular, rabies virus glycoprotein G was determined by ELISA using standard techniques. The affinity of the anti-rabies virus antibodies for rabies virus glycoprotein G can also be measured with a Biacore® instrument, which detects biomolecular binding interactions with surface plasmon resonance technology. Each antibody is added to protein A-coated sensor chips, and rabies virus glycoprotein G is allowed to flow over the chip to measure binding. Binding constants ranging from a $K_D$ of $1\times10^{-6}$M, $K_D$ of $1\times10^{-7}$M, $K_D$ of $1\times10^{-8}$M, $K_D$ of $1\times10^{-9}$M. $K_D$ of $1\times10^{-10}$M. $K_D$ of $1\times10^{-11}$M, $K_D$ of $1\times10^{-12}$M, and higher (or internals or ranges thereof), can be determined. Anti-rabies virus antibodies with favorable binding constants indicate that the antibodies have affinities suitable for use in human therapy.

The antibody 17C7, when tested on the ectodomain region of a rabies G glycoprotein (codon-optimized), was determined by Biacore analysis to have a binding affinity of at least 1.36E-8 M.

Example 3

Rabies Virus Neutralization by Anti-Rabies Virus Antibodies

Antibodies expressed by 17C7, 6G11, 5G5, 2B10, and 1E5 hybridomas were tested for rabies virus neutralization activity in vitro in a series of experiments (see Tables 8-11, below).

Specifically, rabies neutralizing activity was determined using the Rapid Fluorescent Focus Inhibition Test (RFFIT), which detects rabies virus infection of mouse neuroblastoma cells using fluorescent-labeled antibodies. The RFFIT assay is a standardized assay that is used by medical and public heath experts to determine the potency of a given antibody preparation to neutralize rabies viruses (i.e., inhibit its ability to infect cells). The assay is typically performed using a fixed virus (CVS11) but may also be done using isolates from infected animals. The assay is done by the addition of a standard amount of virus with and without antibody dilutions to monolayers of mouse neuroblastoma cells. The monolayers are incubated then foci of infected neuroblastoma cells are detected using a fluorescent-labeled anti-rabies nucleoprotein monoclonal antibody. The foci are visualized and counted using fluorescent microscopy. Subsequent results are reported as the antibody concentration (dilution) where the number of microscope fields without fluorescent foci is 50%. All assays include a standard rabies immune globulin preparation (SRIG) for comparison. Anti-rabies human monoclonal antibodies 17C7, 6G11, 5G5, 2B10, and 1E5 were tested against a panel of rabies virus isolates of public health significance from various vertebrate animals from North America.

Table 8 shows the results of in vitro neutralization assays of selected antibodies, as compared to current therapies (i.e., human anti-rabies serum; "SRIG"), against a panel of rabies virus isolates. Numbers indicate the fold dilution by which an antibody can be diluted and still exhibit a 50% neutralization activity, i.e., the ability to block rabies virus infection of murine neuroblastoma cells in vitro. Results for 17C7 at a higher concentration against selected isolates and are shown in the lower panel.

TABLE 8

Strain Neutralization Results

| | SRIG | 17C7 supernatant or 2 mg/ml* | 6G11 1 mg/ml | 5G5 2 IU/ml or 1 mg/ml* | 1E5 2 IU/ml or 1 mg/ml* | 2B10 2 IU/ml or 1 mg/ml* |
|---|---|---|---|---|---|---|
| rabies virus | | | | | | |
| CVS-11 | 145 | 1100 | 230 | ≧1400* | ≧1400* | ≧1400* |
| ERA | 85 | >1400 | ≧1400 | 230 | 250 | 230 |
| Pasteur virus | 17 | >1400 | 1100 | 95 | 145 | 65 |
| Raccoon, SE US | 110 | >1400 | 1300 | ≧1400* | ≧1400* | ≧1400* |
| Gray fox, TX | 54 | >1400 | 1100 | 95 | 95 | 110 |
| Gray fox, AZ | 50 | >1400 | 1300 | 480 | 480 | 230 |
| Arctic Fox, AK | 54 | >1400 | 1200 | 1000* | 800* | ≧1400* |
| Coyote, TX | 95 | >1400 | 1200 | 60 | 60 | 60 |
| Dog/Coyote, TX | 50 | >1400 | 1100 | 60 | 60 | 75 |
| Skunk, north central | 170 | 200 | 210 | 230 | 250 | 270 |
| Skunk, south central | 54 | >1400 | ≧1400 | 1300* | ≧1400* | ≧1400* |
| Skunk, CA | 29 | >1400 | 800 | 1300* | 1200* | ≧1400* |
| Bat, *Lasiurus borealis*, TN | 42 | 320* | <5 | <5* | <5* | 7* |
| Bat, *Eptesicus fuscus-Myotis* spp., CO | 95 | 625 | 200 | 70 | 95 | 60 |
| Bat, *Myotis* spp., WA | 50 | >1400 | 700 | ≧1400* | ≧1400* | ≧1400* |
| Bat, *Lasiurus cinereus*, AZ | 25 | 270* | <5 | <5* | <5* | 85* |
| Bat, *Pipistrellus subflavus*, AL | 29 | 390 | 13 | 36 | 45 | 36 |
| Bat, *Tadarida brasiliensis*, AL | 50 | ≧1400 | 125 | 180 | 210 | 125 |
| Bat, *Lasionycteris noctivagans*, WA | 42 | ≧1300 | 36 | 40 | 25 | 50 |
| Bat, *Eptesicus fuscus*, PA | 11 | ≧1400 | <5 | 11 | 16 | 29 |
| Mongoose, NY/Puerto Rico | 230 | ≧1400 | ≧1400 | 320 | 390 | 250 |
| Dog, Argentina | 54 | ≧1400 | ≧1400 | 1300* | 1200* | 1300* |
| Dog, Sonora | 56 | ≧1400 | ≧1400 | 19 | 33 | 56 |
| Dog, Gabon | 54 | ≧1400 | ≧1400 | 45 | 19 | 50 |
| Dog, Thai | 56 | ≧1400 | ≧1400 | 17 | 14 | 40 |
| non rabies lyysavirus | | | | | | |
| Lagos | <5 | <5* | nd | nd | nd | nd |
| Mokola | <5 | <5* | nd | nd | nd | nd |
| Duvenhage | 13 | <5* | nd | nd | nd | nd |
| European bat virus 1 | 42 | <5* | nd | nd | nd | nd |
| European bat virus 2 | 40 | <5* | nd | nd | nd | nd |
| Australian bat virus | 54 | >1400* | nd | nd | nd | nd |

Initially, each of the HuMAbs was screened for the ability to neutralize the rabies virus strain CVS-11. Neutralizing HuMabs were then tested more extensively against a broad panel of isolates of public health significance from North and South America, Europe, Africa and Asia. Strikingly, HuMab 17C7 neutralized the majority of rabies virus isolates in contrast to HuMabs 2B10 and 5G5 (Table 8). The 50% end point neutralization titer was determined for one of the street rabies viruses, isolated from a Skunk in California, USA (Skunk-CA). The titer calculated for HuMab17C7 (concentration tested was 0.03 mg/ml) against California Skunk was 1:12,898, which demonstrates that HuMab 17C7 potently neutralizes this street virus.

To better understand how the potency of a single human monoclonal antibody compares to polyclonal hRIG, HuMab 17C7 and hRIG were tested at identical antibody concentrations in a RFFIT assay using the CVS-11 rabies virus. The 50% endpoint titer for hRIG was 1:224, while it was 1:7029 for HuMab 17C7 (FIG. 4). Therefore, HuMab 17C7 inhibited infection by CVS-11 more potently than hRIG at equivalent antibody concentrations. These initial experiments revealed that HuMab 17C7 was able to neutralize many isolates of rabies virus, and that the extent of neutralization ranged from the potent neutralization of the Skunk, CA isolate at a low antibody dose (0.03 ug/ml; 1:12,898) as compared to the less potent neutralization of CVS-11 at higher antibody dose (2 mg/ml; 1:7029).

Repeat testing was done using purified 17C7 at varying concentrations against rabies isolates that did not initially show neutralization in RFFIT testing on hybridoma supernatants (*Lasiurus borealis*, TN and *Lasiurus cinereus*, AZ) and demonstrated to be capable of neutralizing both viruses in the repeat assay. These data imply that HuMab 17C7 interacts with a neutralizing epitope on the rabies glycoprotein from the *L. borealis*-TN and *L. cinereus*-AZ isolates (Table 9).

TABLE 9

50% End Point Neutralization (Reciprocal Titer) of HuMabs 2B10, 17C7 and 5G5 in RFFITs Against Rabies Virus Isolated from North American Bats (*Lasirius borealis* and *cinereus*)

| Rabies Isolate | hRIG (2 IU/ml) | 17C7 (2 mg/ml) | 2B10 (1.5 mg/ml) | 5G5 (1 mg/ml) |
|---|---|---|---|---|
| Bat, *Lasiurus borealis*, TN | 42 | 320 | 7 | <5 |
| Bat, *Lasiurus cinereus*, AZ | 25 | 270 | 85 | <5 |

The HuMab 17C7 clone was also tested for its ability to neutralize non-rabies lyssaviruses. Lyssaviruses are not a significant world-wide public health problem, but have caused fatal disease in a small number of human cases. These occurrences, as well as the prevalence of some lyssaviruses in wild-life reservoirs, have led to a recent interest in whether rabies biologics protect against non-rabies lyssaviruses. HuMab 17C7 was able to potently neutralize Australian bat lyssavirus when tested in a modified RFFIT assay. The titer calculated for HuMab17C7 (concentration tested was 2 mg/ml) against Australian bat lyssavirus was greater than 1:1400 which demonstrates that HuMab 17C7 neutralizes the Australian bat lyssavirus (Table 10).

TABLE 10

50% End Point Neutralization (Reciprocal Titer) of HuMab 17C7 in RFFITs Against Lyssaviruses.

| Lyssavirus | hRIG (2 IU/ml) | HuMab 17C7 (2 mg/ml) |
|---|---|---|
| Rabies (CVS-11) | 270 | >1400 |
| Lagos | <5 | <5 |
| Mokola | <5 | <5 |
| Duvenhage | 13 | <5 |
| European bat lyssavirus 1 | 42 | <5 |
| European bat lyssavirus 2 | 40 | <5 |
| Australian bat lyssavirus | 54 | >1400 |

These data show that that the anti-rabies monoclonal antibodies were capable of neutralizing rabies virus isolates from a variety of North American vertebrate animals of public health significance in the RFFIT assay.

Example 4

Epitope Mapping of Anti-Rabies Virus G Glycoprotein Antibodies

The epitope of rabies virus glycoprotein G bound by each monoclonal antibody was determined by immunoblotting and immunoprecipitation assays (see FIG. 3).

A full-length synthetic human codon-optimized rabies virus G glycoprotein gene from the ERA rabies virus isolate was constructed using polymerase chain reaction (PCR) and genetic engineering. The gene and deletion derivatives were cloned into pCDNA3.1A (Invitrogen) for expression in human 293T cells. Immunoblot and immunoprecipitation experiments were carried out using standard techniques. Results using recombinantly expressed rabies virus G glycoprotein showed that human monoclonal antibody 17C7 mapped to an epitope within the $NH_3$ terminal 19-422 AA of the ectodomain of the rabies G glycoprotein. Human monoclonal clones 5G5, 2B10, 1E5, did not react in immunoblots with soluble G glycoprotein fragments.

To further test the interaction of HuMab 17C7 with rabies glycoproteins in vitro, the rabies virus glycoproteins from a variety of rabies virus strains and isolates were cloned and expressed. Wild type CVS-11 glycoprotein was initially cloned and expressed from the pcDNA3.1 Myc/His (Invitrogen) mammalian expression vector and but at low levels in transfected human cells. To overcome this low level of expression, a codon-optimized version of the ERA rabies glycoprotein-encoding gene (era-co) was engineered using art recognized techniques. Other G proteins were also cloned (ERA era-n), a Skunk isolate from California, USA (skunk-ca), and the bat isolates *l borealis*-tn and *l. cinereus*-az). Codon-optimization of the ERA glycoprotein-encoding gene led to a marked increase in the expression level as compared to wild type ERA glycoprotein (FIG. 5A), and served as a useful reagent for many subsequent experiments.

HuMab 17C7 was determined to immunoprecipitate the glycoproteins from solubilized cells transfected with era-co (not shown), era-n, skunk-ca, *l borealis*-tn and *l. cinereus*-az isolates (FIG. 5B). Using flow cytometry it was further shown that HuMab 17C7 also bound dose dependently to cells expressing the ERA-CO, ERA-N, *L. borealis*-TN and *L. cinereus*-AZ glycoproteins on their cell surface (FIGS. 5C and D). These data show that HuMab 17C7 binds specifically to rabies virus glycoproteins from multiple strains and isolates.

To better characterize the epitope that HuMab 17C7 recognizes, 17C7 was tested and determined to recognized a soluble version of the rabies glycoprotein (amino acids 20-439) that did not possess the cytoplasmic or transmembrane domains of the glycoprotein. HuMAb 17C7 was also determined to recognized a secreted, soluble form of the ERA glycoprotein (ERA-CO20-439) and the CVS-11 glycoprotein (CVS-1120-439) spanning amino acids 20-439 in ELISA (FIG. 6A). Surprisingly, HuMab 17C7 recognized denatured ERA-CO20-439 and ERACO in an SDS-PAGE gel after incubation in sample buffer containing reducing agents and SDS. However, the robustness of the signal was greatly enhanced when the samples were prepared without the addition of reducing agents (FIG. 6B).

This recognition in SDS-PAGE was not observed for CVS-1120-439 glycoprotein without reducing agents (FIG. 6C). These data indicate that HuMab 17C7 recognizes a discontinuous epitope on the ERA rabies glycoprotein. HuMab 17C7 recognizes minor site a and antigenic site III of the rabies virus glycoprotein.

To better understand which regions on the rabies glycoprotein are recognized by HuMab 17C7, rabies viruses capable of growing in the presence of HuMab 17C7 were engineered. In order to create HuMab 17C7 resistant viruses a CVS-11 strain and the Skunk-CA isolate were cell cultured adapted. HuMab 17C7 resistant viruses from the CVS-11 virus stocks were isolated. Analysis of the glycoprotein-encoding sequences of these CVS-11 derived viruses revealed 3-point mutations in the 8 viruses analyzed (CVS1 through 8). Interestingly, in two cases amino acid changes at Asparagine 336, were identified. One virus contained a Asn to Lys change, and multiple viruses contained an Asn to Asp change. Two of the viruses contained an Asn to Asp change at 336, as well as a Gln to Lys change at 426. Asparagine 336 is within a region previously identified as part of antigenic site III (Table 11).

Figure 5:
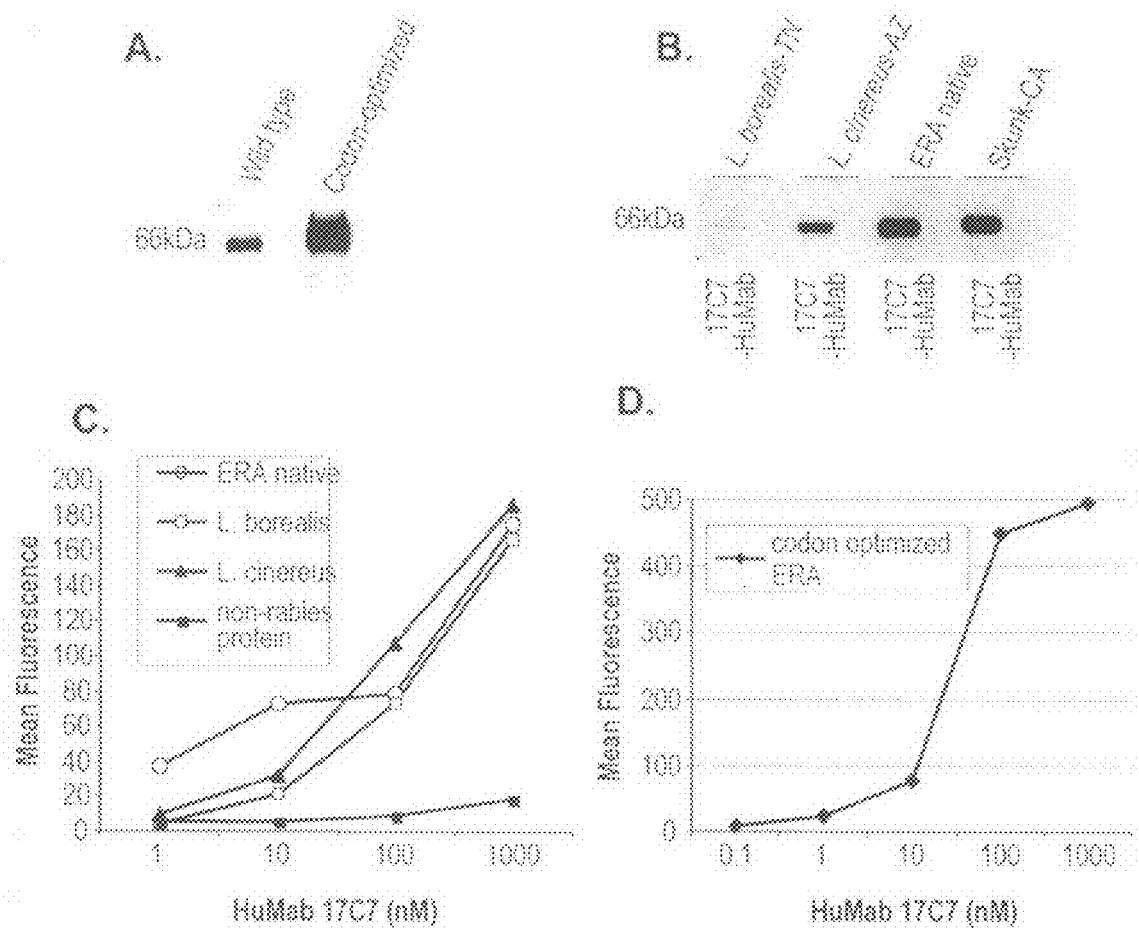
FIG. 5 ERA-N and ERA-CO glycoproteins were expressed in 293T cells and readily expressed when codon optimized (A) and capable of being bound by 17C7 (B-D) when expressed on the surface of cells.
Figure 6:
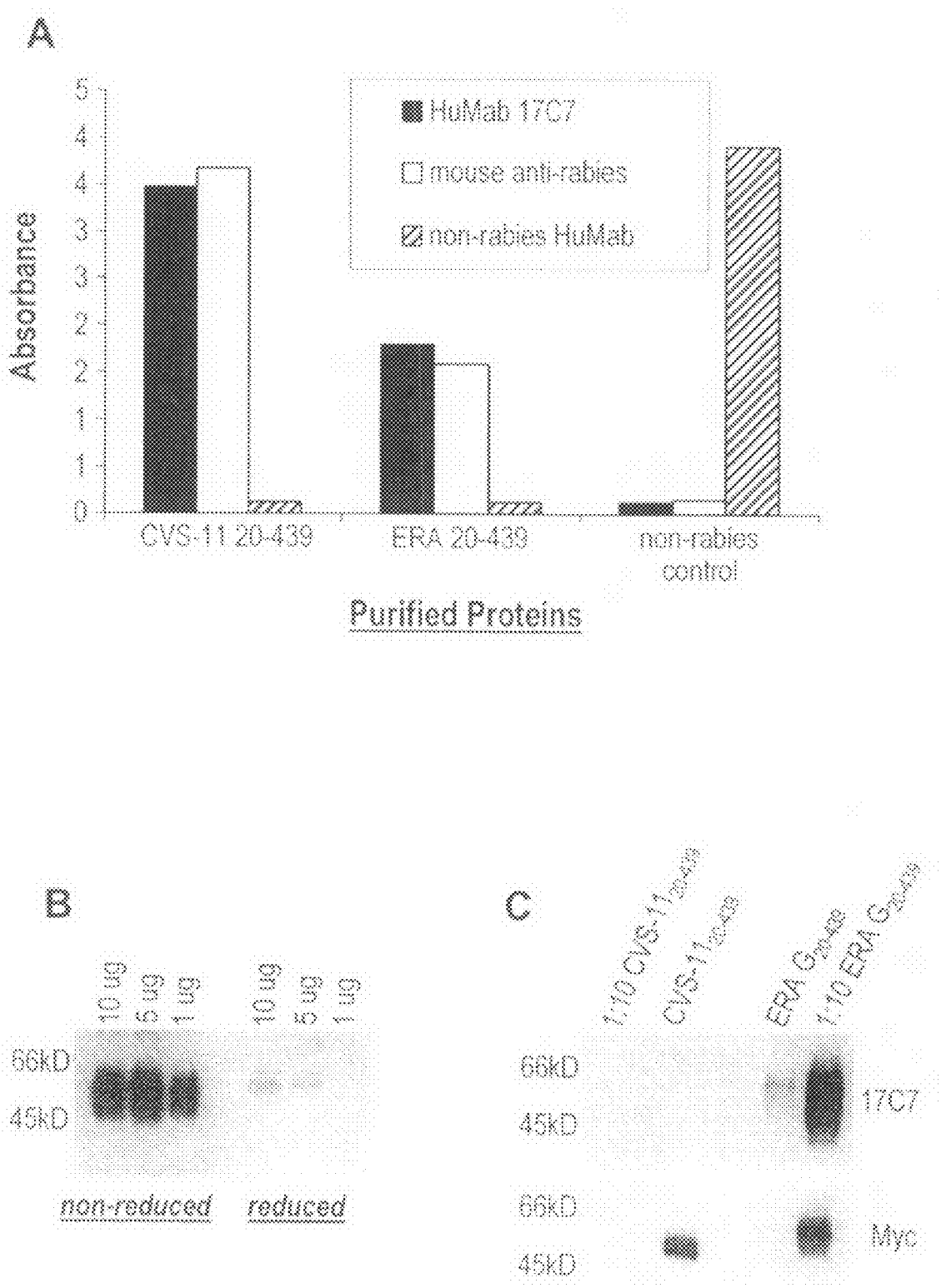
FIG. 6 shows that HuMab 17C7 recognizes the rabies G ectodomain (A) and under non-reducing conditions (B) as well as the G protein of strain ERA (C).

In order to address whether Asparagine 336 was a residue critical for HuMab 17C7 binding, an Asparagine 336 residue in the ERA-co construct to those observed in the CVS-11- derived resistant viruses was mutated. The ERA glycoprotein, as described in FIGS. 5 and 6, is robustly recognized by HuMab 17C7; and the ERA virus, which is highly similar in glycoprotein sequence to Skunk-CA is also potently neutralized by HuMab 17C7 as compared to CVS-11. Therefore, in this set of experiments the Asp 336 residue was shown to be important for HuMab 17C7 neutralization of the CVS-11 virus and also important for maintaining the HuMab 17C7 epitope within the ERA glycoprotein. The mutated glycoproteins ERA-CO N336K and ERA-CO N336D were expressed and assayed for recognition by HuMab 17C7. The mutant glycoproteins were recognized by HuMab 17C7 in an ELISA, however HuMab 17C7 binding to the ERA-CO N336K glycoprotein was greatly reduced compared to wild type (FIG. 7A). The levels of wild type and mutant glycoprotein captured in the ELISA assay were similar, as shown by comparable binding of a mouse anti-rabies glycoprotein monoclonal antibody (FIG. 7A). The mutant glycoproteins were all the appropriate molecular weights, as shown by immunoprecipitation using the His tag, followed by immunoblot analysis with a Myc tag antibody (FIG. 7B). HuMab 17C7 immunoprecipitated the ERA-CO and ERA-CO N336D glycoproteins more readily than the ERA-CO N336K glycoprotein (FIG. 7B), which is consistent with the diminished binding of ERA-CO N336K observed in the ELISA. In contrast to wild type ERA-CO, the mutant proteins were not recognized in Western blot under non-reducing conditions (FIG. 7B). We also created ERA-CO N336D Q426K and ERA Q426K, and the ELISA and immunoblot results were similar to those for ERA-CO N336D, and ERA-CO Q426K respectively, revealing that the Q426K mutation did not affect HuMab 17C7 binding.

Figure 8:
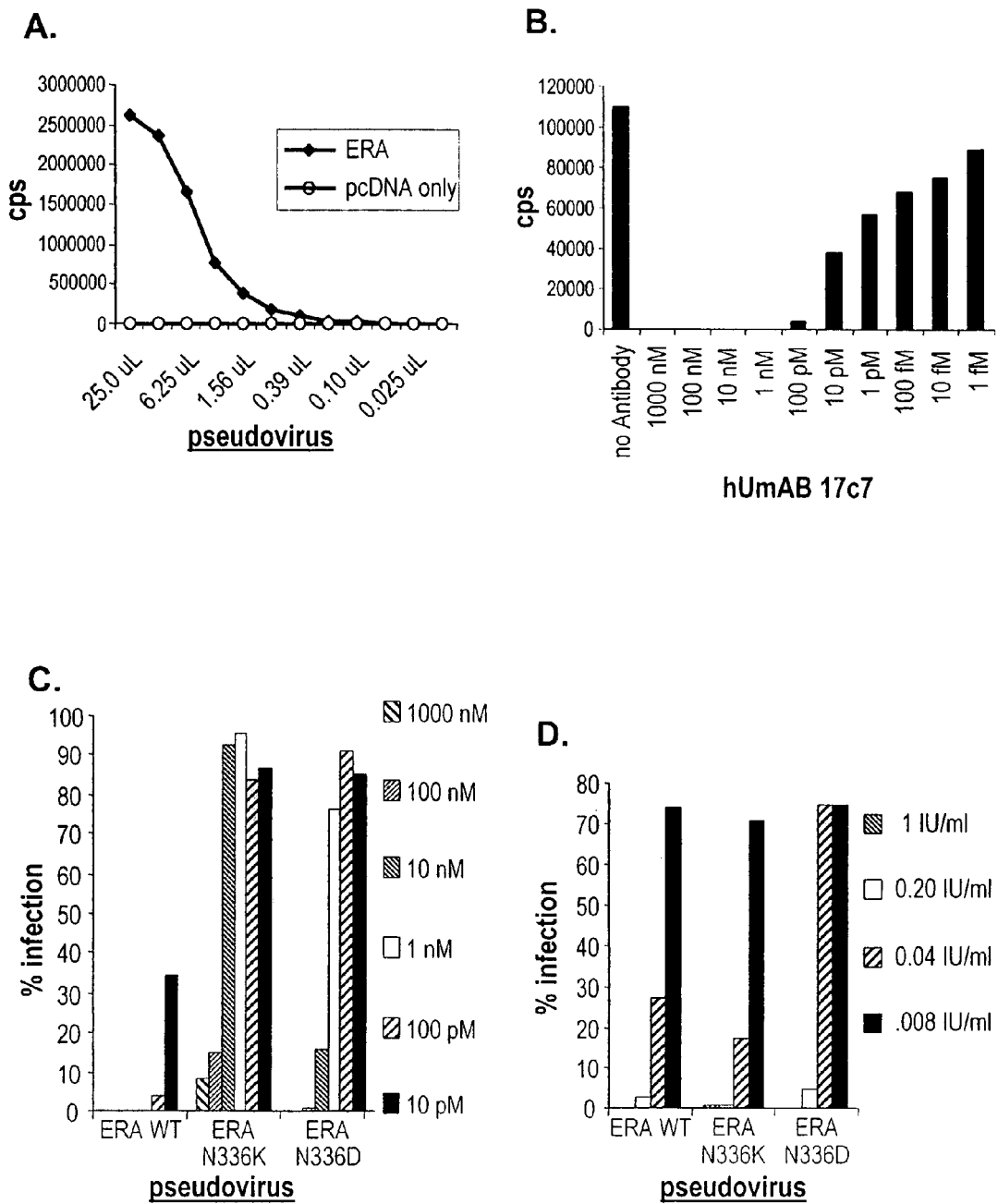
FIG. 8 shows that HuMab 17C7 neutralizes ERA pseudovirus infection of cells (A-B) and the consequences of various mutations to the ERA G protein (C-D) regarding 17C7 binding thereto.

In order to address whether recognition by HuMab 17C7 correlated with neutralization activity, a rabies glycoprotein pseudotyped HIV-1 pseudovirus (10, 20), using the ERA-CO glycoprotein was created. It was observed that these pseudovirus particles infected human cells (FIG. 8A), and that HuMab 17C7 potently inhibited infection by wild type ERA-CO pseudovirus, showing significant inhibition down to 100 pM (FIG. 8B). Unrelated non-rabies HuMabs were tested at 1000 nM and did not neutralize rabies pseudovirus. Interestingly, HuMab 17C7 also inhibited infection of the ERA-CO N336K and ERA-CO N336D pseudoviruses (FIG. 8C), consistent with the observation that HuMab 17C7 recognizes ERA-CO N336K and ERA-CO N336D glycoproteins.

Similar to HuMab 17C7, hRIG also inhibited all of the rabies pseudoviruses in a dose-dependant manner (FIG. 8D). These data demonstrate that the mutations that render the CVS-11 virus immune to HuMab 17C7 neutralization diminish, but do not abrogate, HuMab 17C7 recognition of the ERA glycoprotein and neutralization of ERA pseudovirus.

In order to test whether other well characterized antigenic sites were recognized by HuMab 17C7 a panel of mutant glycoproteins containing amino acid changes previously reported for mAb-resistant viruses altered in residues affecting antigenic sites I, II, III and minor site a were created (Table 11). HuMab 17C7 readily immunoprecipitated all of the mutant glycoproteins from cell lysates with the exception of the R333I, K342T, G343E glycoprotein, which was mutated in a portion of antigenic site III (a.a. 333) and minor site a (a.a. 342 and 343). It was further characterized that the determinant important for HuMab 17C7 binding by creating a separate R333I site III mutant and K342T, G343E minor site a mutant. The R333I site III mutant was recognized by HuMab 17C7 in ELISA and immunoblot, while the K342T, G343E minor a and the R333I, K342T, G343E site III/minor a mutants were less well recognized 19 (FIGS. 9A and B). The K342T, G343E and the R333I, K342T, G343E mutants were recognized by a commercial rabies monoclonal antibody (FIG. 9A), and were the appropriate molecular weight (FIG. 9B), indicating that the glycoproteins were expressed at comparable levels. Therefore, it was determined that the lack of HuMab 17C7 binding to the minor site a mutants was due to mutations in amino acids 342 and 343 of the glycoprotein, demonstrating that these amino acids are important for HuMab 17C7 recognition of the rabies glycoprotein (Table 12).

In addition, the glycoprotein sequences of rabies virus isolates and non-rabies lyssaviruses at amino acids 336, 342 and 343 were compared. The residues important for HuMab 17C7 are conserved between divergent strains of rabies virus and Australian bat lyssavirus, but not other lyssaviruses (Table 13). The glycoprotein sequences of 154 rabies viruses were compared from human, bat and carnivore isolates from all over the world, including North and South America, China and India. Sequence comparison revealed that Asparagine 336 was 93% conserved, Lysine 342 was 98% conserved and Glycine 343 was 99% conserved. These data indicate that residues important for HuMab 17C7 recognition of rabies virus glycoprotein are highly conserved.

TABLE 11

HuMab 17C7 Resistant Viruses

| Virus | Amino acid number | Amino Acid change | Codon Change | Proximity to antigenic site |
|---|---|---|---|---|
| CVS1 | 336 | Asn to Lys | AAT to AAG | III |
| CVS2-6 | 336 | Asn to Asp | AAT to GAT | III |
| CVS7-8 | 336 | Asn to Asp | AAT to GAT | III |
| CVS7-8 | 426 | Glu to Asp | CAG to AAG | N/A |

TABLE 12

HuMab 17C7 Recognizes Site I And Site II Mutated Glycoproteins

| Mutations in recombinant glycoprotein | HuMab 17C7 binding | Antigenic sites |
|---|---|---|
| R333I | + | III |
| K342T, G343E | − | Minor a |
| R333I, K342T, G343E | − | Minor a and III |
| K226E, L231P | + | I |
| G34E | + | II |
| G40V, S42P, M44I | + | II |
| K198E | + | II |

TABLE 13

Amino Acids 330-345 of Rabies Viruses and Other Lyssaviruses

| Virus | Genbank ID | Amino acids 330-345 |
|---|---|---|
| CVS-11 | AF085333 | KSVRTWNEIIPSKGCL |
| ERA-CO | AF406693 | KSVRTWNEILPSKGCL |
| Skunk-CA | N/A | KSVRTWNEILPSKGCL |
| L. borealis-TN | N/A | KSVKTWNEVIPSKGCL |
| L. cinereus-AZ | N/A | KSVKTWNEVIPSKGCL |
| ERA native | N/A | KSVRTWNEIIPSKGCL |
| ABLV | AF406693 | KSVRTWNEIIPSKGCL |
| EBLV-1 | AF298143 | KSVREWTEVIPSKGCL |
| EBLV-2 | AF298145 | KSIREWTDVIPSKGCL |
| Lagos | AF429312 | LKVDNWSEILPSKGCL |
| Mokola | MVU17064 | KRVDRWADILPSRGCL |

HuMab 17C7 recognizes a discontinuous epitope due to its ability to bind with greater reactivity with non-reduced protein. The interaction of HuMab 17C7 with the rabies glycoprotein is also unique because it is able to immunoprecipitate membrane bound glycoproteins of a variety of rabies isolates, and to neutralize all of these isolates, but is only able to interact with a subset of secreted soluble glycoproteins in ELISA and immunoblots.

The recognition of non-reduced protein by HuMab 17C7 indicates that antigenic site II, minor site a, or an unknown conformational determinant of the rabies glycoprotein is important for recognition by HuMab 17C7. The analysis of mutant glycoproteins revealed that 2 amino acid changes at minor site a dramatically decreased HuMab 17C7 recognition of the rabies glycoprotein. These two amino acid changes disrupted the HuMab 17C7-binding site on the rabies glycoprotein and/or result in a modification of the rabies glycoprotein tertiary structure critical for HuMab 17C7 binding.

These data show that HuMab 17C7 resistant viruses indicate that Asparagine 336 is important for HuMab 17C7 neutralization. The amino acid change at residue 336 disrupts the HuMab 17C7-binding site on the rabies glycoprotein and/or results in a modification of the rabies glycoprotein structure critical for HuMab 17C7 binding.

The analysis of mutant glycoproteins created with site-directed mutagenesis also revealed that HuMab 17C7 recognizes both minor site a and part of antigenic site III.

Taken together these results indicate that HuMab 17C7 recognizes an epitope that is broadly conserved. The broad cross reactivity of HuMab 17C7 indicates that it can be used in place of RIG for post exposure prophylaxis.

Example 5

Protection of Hamsters from Lethal Rabies Virus Challenge by Administration of Anti-Rabies Virus Antibodies Antibodies were tested for the ability to protect hamsters from challenge with a lethal dose of rabies virus (see Tables 14-15).

The human monoclonal antibody 17C7 was also tested in a hamster model of post exposure prophylaxis (PEP) to determine its potential as a prophylaxis for rabies virus infection in humans. Hamsters were challenged in the gastrocnemius muscle of the hind leg with a fatal dose of rabies virus. The challenge virus was originally isolated from a Texas coyote. In this model, untreated animals die of rabies virus infection in less than two weeks.

Briefly, animals were challenged in the gastrocnemius muscle with 50 μl of rabies virus and given anti-rabies virus antibodies in the same site 24 hours later. Animals (n=9) were treated with a single dose of 19 mg/kg of commercially available human rabies serum derived immunoglobulin (HRIG, Imogam, Aventis) or human monoclonal antibody 17C7 at various doses (5, 0.5 or 0.25 mg/kg). All animals in an untreated challenge group died of rabies within 2 weeks of challenge. The percent survival at 63 days after challenge showed better protection by the monoclonal antibody at a dose of 0.25 mg/kg than commercially available human immunoglobulin (Table 14).

A similar experiment was conducted where animals were treated with antibody post exposure to rabies and, in addition, treated with rabies vaccine. Commercial human vaccine was administered in the opposite gastrocnemius muscle from the challenge site in a 50 μl injection volume 1, 3, 7, 14 and 28 days after rabies challenge. Antibodies were administered as described previously. Again, the percent survival at 53 days after challenge showed better protection by the monoclonal antibody at a dose of 0.125 mg/kg than commercially available human immunoglobulin (Table 15).

Antibody was administered alone and with vaccine and results shown in Tables 14-15 demonstrate that hamsters challenged with a lethal dose of rabies virus can be protected with antibodies of the invention given after exposure to the virus either alone (see Table 14) or in conjunction with the administration of a rabies vaccine (Table 15).

To demonstrate that 17C7 does not interfere with vaccine response, hamsters were given 17C7 and rabies vaccine. As shown in Table 16, the animals responded to vaccine even when given 17C7, thereby demonstrating that the 17C7 antibody does not interfere with vaccine response.

TABLE 14

Post exposure protection from rabies with a human monoclonal antibody[a]

| Sample | IU/kg | mg/kg | Survivorship |
|---|---|---|---|
| A human rabies immune globulin | 15 | 8.0 | 5/9 |
| B human rabies immune globulin | 6 | 4.0 | 4/9 |
| C human rabies immune globulin | 1 | 0.4 | 0/9 |
| D human rabies immune globulin | 0.05 | 0.0 | 0/9 |
| E hu MoAb 17C7 | 26 | 1.7 | 9/9 |
| F hu MoAb 17C7 | 7 | 0.9 | 9/9 |
| G hu MoAb 17C7 | 1 | 0.1 | 6/9 |
| H hu MoAb 17C7 | 0.05 | 0.0 | 1/9 |
| I Controls | — | — | 0/9 |

[a] At 24 hrs after inoculation of a Texas coyote rabies virus isolate (#323), prophylaxis was initiated in eight treatment groups of 9 animals each with human monoclonal antibody 17C7 (26 IU/kg; 7 IU/kg, 1 IU/kg or 0.05 IU/kg) or commercial human rabies immune globulin (15 IU/kg, 6 IU/kg, 1 IU/kg or 0.05 IU/kg), administered at the site of virus inoculation. The untreated control group consisted of 9 animals.

TABLE 15

Rabies post-exposure prophylaxis including vaccine: comparison of a human monoclonal antibody to human rabies immune globulin[a]

| Sample | IU/kg | mg/kg | Survivorship at 90 d |
|---|---|---|---|
| A human rabies immune globulin | 20 | 21 | 17/18 |
| B human monoclonal antibody | 20 | 1 | 17/18 |
| C human monoclonal antibody | 10 | 0.5 | 16/18 |
| D human monoclonal antibody | 2 | 0.1 | 16/18 |
| E controls | — | — | 0/18 |

[a] At 24 hrs after rabies virus inoculation (50 ul of a 1:1000 ($10^{6.8}$ MICLD$_{50}$/ml) salivary gland homogenate from a naturally infected coyote (Texas coyote rabies virus isolate #323)), prophylaxis was initiated in four treatment groups (A-D) of 18 hamsters each with human monoclonal antibody 17C7 (20 IU/kg; 10 IU/kg or 2 IU/kg) or commercial human rabies immune globulin (20 IU/kg), administered at the site of virus inoculation. A 50 ul volume of commercial rabies vaccine was administered in the left gastrocnemius muscle. Additional doses of vaccine were administered on days 3, 7, 14 and 28. The untreated control group consisted of 18 animals.

TABLE 16

Geometric Mean Titers of Rabies Virus Neutralizing Antibodies Following Rabies Vaccine and Antibody Combinations

| | Day | | | | |
|---|---|---|---|---|---|
| Groups | 3 | 7 | 14 | 28 | 42 |
| human rabies Ig + vaccine | 15 | 26 | 1,315 | 10,013 | 5,878 |
| +/−St Dev | 9-26 | 13-50 | 1241-1393 | 3730-26873 | 4293-8049 |
| B hu MoAb + vaccine | 12 | 22 | 339 | 4,442 | 6,704 |

TABLE 16-continued

Geometric Mean Titers of Rabies Virus Neutralizing Antibodies Following Rabies Vaccine and Antibody Combinations

| Groups | Day | | | | |
|---|---|---|---|---|---|
| | 3 | 7 | 14 | 28 | 42 |
| +/−St Dev | 8-17 | 11-45 | 129-8889 | 2754-7158 | 6257-7189 |
| C hu MoAb + vaccine | 10 | 17 | 404 | 9,304 | 5,812 |
| +/−St Dev | 9-11 | 9-31 | 181-900 | 1186-21378 | 4708-7161 |

[a]Three treatment groups (A-C) of animals received human monoclonal antibody 17C7 (25 IU/kg (group B) or 15 IU/kg (group C)) or commercial human rabies immune globulin (25 IU/kg) administered intramuscularly in the left gastrocnemius muscle. A 50 ul volume of commercial rabies vaccine was administered in the right gastrocnemius muscle. Additional doses of vaccine were administered on days 3, 7, 14 and 28. On days 3, 7, 14, 28, and 42, six animals per group were sedated, blood was collected, and the animals were euthanized.

Taken together, these data indicate that HuMab 17C7 consistently provides in vivo protection against rabies and can be used in place of RIG for post exposure prophylaxis.

Example 6

Production of Anti-Rabies Virus Antibodies for Administration in Humans

Human antibodies of the present invention can be cloned and recombinantly expressed to facilitate or increase their production using known techniques.

Nucleic acid sequences encoding the variable heavy chain and light chains of an antibody clone of the invention can be cloned into a pIE-Ugamma1F vector using standard recombinant DNA methodology. The vector is amplified in *E. coli*, purified, and transfected into CHO cells. Transfected cells are plated at $4\times10^5$ cells per well in a 96-well dish and selected for vector transfection with G418. Resistant clones selected by G418 resistance, are then assayed along with other transfectomas for production of IgG. The expression of an antibody can be amplified by growth in the presence of increasing concentrations of methotrexate. A culture capable of growth in 175 nM methotrexate is chosen for cloning single cells for further development. Plating the culture in 96 well plates at low density allowed generation of cultures arising from a single cell or clones. The cultures are screened for production of human IgG, and the cell that produces the highest level of IgG is typically selected for further use. The methotrexate-amplified clone is expanded to produce a cell bank including multiple frozen vials of cells. Alternatively, glutamine synthetase (GS) vectors can be used with cell selection achieved using, e.g., methionine sulphoximine (see, e.g., U.S. Pat. Nos. 5,827,739; 5,122,464; 5,879,936; and 5,891,693).

To prepare antibodies from transfected cells, cells from a clone isolated in the previous steps are cultured and expanded as inoculum for a bioreactor. The bioreactor typically holds a 500 liter volume of culture medium. The cells are cultured in the bioreactor until cell viability drops, which indicates a maximal antibody concentration has been produced in the culture. The cells are removed by filtration. The filtrate is applied to a protein A column. Antibodies bind to the column, and are eluted with a low pH wash. Next, the antibodies are applied to a Q-Sepharose column to remove residual contaminants, such as CHO cell proteins, DNA, and other contaminants (e.g., viral contaminants, if present). Antibodies are eluted from the Q-Sepharose column, nano-filtered, concentrated, and washed in a buffer such as PBS. The preparation is then aseptically aliquoted into vials for administration.

Other Embodiments

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated monoclonal antibody or antigen binding portion thereof that binds to rabies virus G protein, comprising a variable heavy chain region comprising SEQ ID NO: 1.

2. An isolated monoclonal antibody or antigen binding portion thereof that binds to rabies virus G protein, comprising a variable light chain region comprising SEQ ID NO: 2.

3. An isolated monoclonal antibody or antigen binding portion thereof that binds to rabies virus G protein, comprising a variable heavy chain region comprising SEQ ID NO: 1 and a variable light chain region comprising SEQ ID NO:2.

4. An isolated monoclonal antibody or antigen binding portion thereof that binds to rabies virus G protein, comprising:

(a) the heavy chain variable region CDR3 sequence comprises SEQ ID NO:5;

(b) the light chain variable region CDR3 sequence comprises SEQ ID NO:8;

(c) the heavy chain variable region CDR2 sequence comprises SEQ ID NO:4;

(d) the light chain variable region CDR2 sequence comprises SEQ ID NO:7;

(e) the heavy chain variable region CDR1 sequence comprises SEQ ID NO:3; and (f) the light chain variable region CDR1 sequence comprises SEQ ID NO: 6.

5. The antibody or antigen binding portion thereof of any one of claims 1-3 or 4, wherein the antibody or antigen binding portion thereof inhibits binding of rabies virus to mammalian cells.

6. The antibody or antigen binding portion thereof of any one of claims 1-3 or 4, wherein the antibody or antigen binding portion thereof inhibits binding of rabies virus G protein to mammalian cells.

7. The antibody of any one of claims 1-3 or 4, wherein the antibody is a full-length antibody.

8. An isolated polypeptide comprising the antigen binding portion of an antibody of any one of claims 1-3 or 4.

9. The antibody or antigen binding portion thereof of any one of claims 1-3 or 4, wherein the antibody or antigen binding portion thereof comprises an effector domain.

10. The antibody or antigen binding portion thereof of any one of claims 1-3 or 4, wherein the antibody or antigen binding portion thereof comprises an FC domain.

11. The antibody or antigen binding portion thereof of any one of claims 1-3 or 4, wherein the antibody or antigen binding portion thereof is a single-chain antibody.

12. The antibody or antigen binding portion thereof of any one of claims 1-3 or 4, wherein the antibody or antigen binding portion thereof is a Fab fragment.

13. The antibody or antigen binding portion thereof of any one of claims 1-3 or 4, further comprising a label or toxin.

14. A composition comprising the antibody or antigen binding portion of any one of claims 1-3 or 4 in a pharmaceutically acceptable carrier.

15. A kit comprising one or more isolated monoclonal antibodies or antigen binding portions thereof as recited in any one of claims 1-3 or 4, and instructions for use in treating rabies virus-mediated disease.

16. A method of treating rabies virus disease in a subject, the method comprising: administering to the subject an isolated monoclonal antibody or antigen binding portion thereof of any one of claims 1-3 or 4, in an amount effective to inhibit a symptom of rabies virus disease.

17. The method of claim 16, wherein the subject is human.

18. The method of claim 16, wherein the antibody or antigen binding portion thereof is administered intravenously, intramuscularly, or subcutaneously to the subject.

19. The method of claim 16, wherein the antibody or antigen binding portion thereof is administered in combination with a second therapeutic agent.

20. The method of claim 19, wherein the second agent is an antibody or antigen binding portion thereof.

21. The method of claim 19, wherein the second agent is an antiviral agent.

22. The method of claim 19, wherein the second agent is a rabies virus vaccine.

23. The method of claim 22, wherein rabies virus vaccine is a rabies virus G protein or fragment thereof.

24. A composition suitable for treating a rabies virus-associated disease or disorder in a mammal comprising an antibody or antigen binding fragment of any one of claims 1-3 or 4, in a pharmaceutically acceptable carrier.

25. The composition of claim 24, wherein the composition further comprises a second antibody that binds rabies virus.

26. A method of treating rabies a virus-associated disease or disorder in a mammal comprising, administering to the mammal two or more antibodies or fragments thereof of any one of claims 1-3 or 4, such that infectivity of cells by rabies virus is inhibited.

* * * * *